US012805934B2

(12) United States Patent
Cook et al.

(10) Patent No.: US 12,805,934 B2
(45) Date of Patent: Nov. 24, 2026

(54) OPTICAL ASSEMBLIES TO IMPROVE ENERGY COUPLING TO PRESSURE WAVE GENERATOR OF AN INTRAVASCULAR LITHOTRIPSY DEVICE

(71) Applicant: Boston Scientific Scimed, Inc., Maple Grove, MN (US)

(72) Inventors: Christopher A. Cook, Laguna Niguel, CA (US); Eric Schultheis, San Clemente, CA (US); Mina Mossayebi, Irvine, CA (US); George Liu, Irvine, CA (US); Itzhak Fang, Irvine, CA (US); Jennet Johnson, Fallbrook, CA (US); Theresa Shar, San Diego, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 287 days.

(21) Appl. No.: 17/666,172

(22) Filed: Feb. 7, 2022

(65) Prior Publication Data

US 2022/0249165 A1 Aug. 11, 2022

Related U.S. Application Data

(60) Provisional application No. 63/148,133, filed on Feb. 10, 2021.

(51) Int. Cl.
*A61B 18/26* (2006.01)
*A61B 18/00* (2006.01)
(Continued)

(52) U.S. Cl.
CPC ............ *A61B 18/26* (2013.01); *A61B 18/245* (2013.01); *A61B 2018/0022* (2013.01);
(Continued)

(58) Field of Classification Search
CPC .................. A61B 18/26; A61B 18/245; A61B 2018/0022; A61B 2018/00369;
(Continued)

(56) References Cited

U.S. PATENT DOCUMENTS 4,649,924 A 3/1987 Taccardi
4,699,147 A 10/1987 Chilson et al.
(Continued)

FOREIGN PATENT DOCUMENTS

AU 2017205323 1/2022
AU 2019452180 1/2022
(Continued)

OTHER PUBLICATIONS

Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.
(Continued)

*Primary Examiner* — Amanda L Steinberg
*Assistant Examiner* — Laura Hodge
(74) *Attorney, Agent, or Firm* — SEAGER, TUFTE & WICKHEM, LLP

(57) ABSTRACT

A catheter system (100) for treating a treatment site (106) within or adjacent to a vessel wall (108) or a heart valve includes an inflatable balloon (104), an optical fiber (122), and an energy source (124). The optical fiber (122) has a fiber proximal end (122P), and a fiber distal end (122D) positioned within the inflatable balloon (104). The optical fiber (122) is configured to receive an energy pulse so that the optical fiber (122) emits light energy in a direction away from the optical fiber (122) to generate a plasma pulse within the inflatable balloon (104). The optical fiber (122) can be tapered from the fiber proximal end (122P) toward the fiber
(Continued)

distal end (122D). The energy source (124) in optical communication with the fiber proximal end (122P) of the optical fiber (122), and can include a laser. The optical fiber (122) includes a first fiber member (250) and a second fiber member (258) that is coupled to the first fiber member (250). The first fiber member (250) can be fused to the second fiber member (258) in a fused region (256). The first fiber member (250) and the second fiber member (258) can be formed as a unitary structure. The catheter system (100) can also include a ferrule (248) that encircles the fused region (256).

17 Claims, 7 Drawing Sheets

(51) Int. Cl.
*A61B 18/04* (2006.01)
*A61B 18/20* (2006.01)
*A61B 18/22* (2006.01)
*A61B 18/24* (2006.01)

(52) U.S. Cl.
CPC ............... *A61B 2018/00369* (2013.01); *A61B 2018/0041* (2013.01); *A61B 18/042* (2013.01); *A61B 2018/2035* (2013.01); *A61B 2018/2205* (2013.01); *A61B 2018/2211* (2013.01); *A61B 2018/263* (2013.01); *A61B 2018/266* (2013.01)

(58) Field of Classification Search
CPC .... A61B 2018/0041; A61B 2018/2035; A61B 2018/2205; A61B 2018/2211; A61B 2018/263
See application file for complete search history.

(56) References Cited

U.S. PATENT DOCUMENTS 4,799,479 A 1/1989 Spears
4,850,351 A 7/1989 Herman
4,913,142 A 4/1990 Kittrell et al.
4,932,954 A 6/1990 Wondrazek et al.
4,955,895 A 9/1990 Suglyama
4,960,108 A 10/1990 Reichel et al.
4,994,059 A 2/1991 Kosa et al.
4,998,930 A 3/1991 Lundahl
5,019,075 A 5/1991 Spears et al.
5,034,010 A 7/1991 Kittrell et al.
5,041,121 A 8/1991 Wondrazek et al.
5,057,106 A 10/1991 Kasevich et al.
5,082,343 A 1/1992 Coult et al.
5,093,877 A 3/1992 Aita et al.
5,104,391 A 4/1992 Ingle
5,104,392 A 4/1992 Kittrell et al.
5,109,452 A 4/1992 Selvin et al.
5,116,227 A 5/1992 Levy
5,126,165 A 6/1992 Akihama et al.
5,152,768 A 10/1992 Bhatta
5,173,049 A 12/1992 Levy
5,176,674 A 1/1993 Hofmann
5,181,921 A 1/1993 Makita et al.
5,188,632 A * 2/1993 Goldenberg .... A61M 25/09033 606/7
5,200,838 A 4/1993 Nudelman
5,269,777 A 12/1993 Doiron
5,290,277 A 3/1994 Vercimak et al.
5,324,282 A 6/1994 Dodick
5,328,472 A 7/1994 Steinke et al.
5,336,184 A 8/1994 Teirstein
5,363,458 A 11/1994 Pan
5,372,138 A 12/1994 Crowley
5,387,225 A 2/1995 Euteneur
5,400,428 A 3/1995 Grace
5,410,797 A 5/1995 Steinke et al.
5,417,689 A 5/1995 Fine
5,422,926 A 6/1995 Smith
5,431,647 A 7/1995 Purcell
5,454,809 A 10/1995 Janssen
5,456,680 A 10/1995 Taylor
5,474,537 A 12/1995 Solar
5,496,311 A 3/1996 Abele et al.
5,509,917 A 4/1996 Cecchetti
5,519,798 A 5/1996 Shahid
5,540,679 A 7/1996 Fram
5,562,657 A 10/1996 Griffin
5,598,494 A 1/1997 Behrmann et al.
5,609,606 A 3/1997 O'Boyle
5,611,807 A 3/1997 O'Boyle
5,637,877 A 6/1997 Sinofsky
5,661,829 A 8/1997 Zheng
5,697,377 A 12/1997 Wittkamph
5,718,241 A 2/1998 Ben-Haim et al.
5,729,583 A 3/1998 Tang
5,764,843 A 6/1998 Macken et al.
5,772,609 A 6/1998 Nguyen et al.
5,860,974 A 1/1999 Abele
5,891,135 A 4/1999 Jackson et al.
5,906,611 A 5/1999 Dodick et al.
5,944,697 A 8/1999 Benett et al.
6,007,514 A 12/1999 Nita
6,015,404 A 1/2000 Altshuler
6,080,119 A 6/2000 Schwarze et al.
6,123,923 A 9/2000 Unger
6,139,510 A 10/2000 Palermo
6,186,963 B1 2/2001 Schwarze et al.
6,203,537 B1 3/2001 Adrian
6,210,404 B1 4/2001 Shadduck
6,339,470 B1 1/2002 Papademetriou et al.
6,356,575 B1 3/2002 Fukumoto
6,368,318 B1 4/2002 Visuri et al.
6,423,055 B1 7/2002 Farr
6,500,174 B1 12/2002 Maguire et al.
6,514,203 B2 2/2003 Bukshpan
6,514,249 B1 2/2003 Maguire
6,524,251 B2 2/2003 Rabiner et al.
6,538,739 B1 3/2003 Visuri et al.
6,544,218 B1 4/2003 Choi
6,548,010 B1 4/2003 Stivland et al.
6,560,387 B1 5/2003 Hehlen et al.
6,607,502 B1 8/2003 Maguire et al.
6,631,220 B1 10/2003 Liang et al.
6,652,547 B2 11/2003 Rabiner et al.
6,666,834 B2 12/2003 Restle et al.
6,702,781 B1 3/2004 Reifart et al.
6,773,447 B2 8/2004 Laguna
6,824,554 B1 11/2004 Jang
6,849,994 B1 2/2005 White et al.
6,890,317 B2 5/2005 Gerdts et al.
6,947,785 B1 9/2005 Beatty et al.
6,966,890 B2 11/2005 Coyle et al.
6,978,168 B2 12/2005 Beatty et al.
6,990,370 B1 1/2006 Beatty et al.
7,273,470 B2 9/2007 Wantink
7,309,324 B2 12/2007 Hayes et al.
7,367,967 B2 5/2008 Eidenschink
7,470,240 B2 12/2008 Schultheiss et al.
7,539,231 B1 5/2009 Honea et al.
7,569,032 B2 8/2009 Naimark et al.
7,599,588 B2 10/2009 Eberle et al.
7,641,646 B2 1/2010 Kennedy, II
7,691,079 B2 4/2010 Gobel
7,713,260 B2 5/2010 Lessard
7,758,572 B2 7/2010 Weber et al.
7,762,984 B2 7/2010 Kumoyama et al.
7,810,395 B2 10/2010 Zhou
7,850,685 B2 12/2010 Kunis et al.
7,867,178 B2 1/2011 Simnacher
7,909,797 B2 3/2011 Kennedy, II et al.
7,942,850 B2 5/2011 Levit et al.
7,967,781 B2 6/2011 Simpson et al.
7,972,299 B2 7/2011 Carter
7,985,189 B1 7/2011 Ogden et al.
8,021,328 B2 9/2011 Lee

(56) References Cited

U.S. PATENT DOCUMENTS

| | | | |
|---|---|---|---|
| 8,029,473 | B2 | 10/2011 | Carter |
| 8,043,256 | B2 | 10/2011 | Hansen |
| 8,066,732 | B2 | 11/2011 | Paul et al. |
| 8,088,121 | B2 | 1/2012 | Nishide |
| 8,157,760 | B2 | 4/2012 | Criado et al. |
| 8,162,859 | B2 | 4/2012 | Schultheiss et al. |
| 8,166,825 | B2 | 5/2012 | Zhou |
| 8,192,368 | B2 | 6/2012 | Woodruff |
| 8,197,505 | B2 | 6/2012 | Hirszowicz et al. |
| 8,246,643 | B2 | 8/2012 | Nita |
| 8,267,886 | B2 | 9/2012 | Ewing |
| 8,292,913 | B2 | 10/2012 | Warnack |
| 8,328,820 | B2 | 12/2012 | Diamant |
| 8,364,235 | B2 | 1/2013 | Kordis et al. |
| 8,372,034 | B2 | 2/2013 | Levit |
| 8,382,738 | B2 | 2/2013 | Simpson et al. |
| 8,414,527 | B2 | 4/2013 | Mallaby |
| 8,419,613 | B2 | 4/2013 | Saadat |
| 8,439,890 | B2 | 5/2013 | Beyar |
| 8,556,813 | B2 | 10/2013 | Cashman et al. |
| 8,556,851 | B2 | 10/2013 | Hirszowicz |
| 8,574,247 | B2 | 11/2013 | Adams et al. |
| 8,657,814 | B2 | 2/2014 | Werneth |
| 8,709,075 | B2 | 4/2014 | Adams et al. |
| 8,728,091 | B2 | 5/2014 | Hakala et al. |
| 8,734,424 | B2 | 5/2014 | Watanabe |
| 8,747,416 | B2 | 6/2014 | Hakala et al. |
| 8,784,362 | B2 | 7/2014 | Boutilette |
| 8,834,510 | B2 | 9/2014 | Wilson et al. |
| 8,888,788 | B2 | 11/2014 | Hakala et al. |
| 8,956,371 | B2 | 2/2015 | Hawkins et al. |
| 8,956,374 | B2 | 2/2015 | Hawkins et al. |
| 8,986,339 | B2 | 3/2015 | Warnack |
| 8,992,519 | B2 | 3/2015 | Kim et al. |
| 8,992,817 | B2 | 3/2015 | Stamberg |
| 9,005,216 | B2 | 4/2015 | Hakala et al. |
| 9,011,462 | B2 | 4/2015 | Adams et al. |
| 9,011,463 | B2 | 4/2015 | Adams et al. |
| 9,011,511 | B2 | 4/2015 | Gregorich |
| 9,044,575 | B2 | 6/2015 | Beasley et al. |
| 9,044,618 | B2 | 6/2015 | Hawkins et al. |
| 9,044,619 | B2 | 6/2015 | Hawkins et al. |
| 9,056,185 | B2 | 6/2015 | Fischell et al. |
| 9,072,534 | B2 | 7/2015 | Adams et al. |
| 9,089,669 | B2 | 7/2015 | Haslinger et al. |
| 9,131,949 | B2 | 9/2015 | Coleman et al. |
| 9,138,249 | B2 | 9/2015 | Adams et al. |
| 9,138,260 | B2 | 9/2015 | Miller et al. |
| 9,180,280 | B2 | 11/2015 | Hawkins et al. |
| 9,220,521 | B2 | 12/2015 | Hawkins et al. |
| 9,237,984 | B2 | 1/2016 | Hawkins et al. |
| 9,254,169 | B2 | 2/2016 | Long et al. |
| 9,282,984 | B2 | 3/2016 | Nita |
| 9,283,359 | B2 | 3/2016 | Pepper |
| 9,289,132 | B2 | 3/2016 | Ghaffari et al. |
| 9,289,224 | B2 | 3/2016 | Adams et al. |
| 9,289,319 | B2 | 3/2016 | Pacetti et al. |
| 9,320,530 | B2 | 4/2016 | Grace |
| 9,333,000 | B2 | 5/2016 | Hakala et al. |
| 9,339,632 | B2 | 5/2016 | Eidenschink et al. |
| 9,364,645 | B2 | 6/2016 | Erikawa |
| 9,375,223 | B2 | 6/2016 | Wallace |
| 9,421,025 | B2 | 8/2016 | Hawkins et al. |
| 9,433,428 | B2 | 9/2016 | Hakala et al. |
| 9,433,745 | B2 | 9/2016 | Cully |
| 9,504,809 | B2 | 11/2016 | Bo |
| 9,510,887 | B2 | 12/2016 | Burnett |
| 9,522,012 | B2 | 12/2016 | Adams |
| 9,554,815 | B2 | 1/2017 | Adams et al. |
| 9,555,267 | B2 | 1/2017 | Ein-gal |
| 9,566,209 | B2 | 2/2017 | Katragadda et al. |
| 9,579,114 | B2 | 2/2017 | Mantell et al. |
| 9,579,492 | B2 | 2/2017 | Simpson |
| 9,585,684 | B2 | 3/2017 | Nita et al. |
| 9,592,328 | B2 | 3/2017 | Jeevanandam |
| 9,603,506 | B2 | 3/2017 | Goldfarb et al. |
| 9,629,567 | B2 | 4/2017 | Porath et al. |
| 9,642,673 | B2 | 5/2017 | Adams |
| 9,662,069 | B2 | 5/2017 | De Graff et al. |
| 9,687,166 | B2 | 6/2017 | Subramaniam |
| 9,700,655 | B2 | 7/2017 | Laudenslager et al. |
| 9,730,715 | B2 | 8/2017 | Adams |
| 9,737,361 | B2 | 8/2017 | Magana |
| 9,764,142 | B2 | 9/2017 | Imran |
| 9,782,570 | B2 | 10/2017 | Hirszowicz |
| 9,814,476 | B2 | 11/2017 | Adams et al. |
| 9,833,348 | B2 | 12/2017 | Jordan et al. |
| 9,839,764 | B2 | 12/2017 | Chouinard |
| 9,861,377 | B2 | 1/2018 | Mantell et al. |
| 9,867,629 | B2 | 1/2018 | Hawkins et al. |
| 9,878,135 | B2 | 1/2018 | Holzapfel et al. |
| 9,894,756 | B2 | 2/2018 | Weinkam et al. |
| 9,901,704 | B2 | 2/2018 | Appling |
| 9,955,946 | B2 | 5/2018 | Miller et al. |
| 9,974,963 | B2 | 5/2018 | Imran |
| 9,974,970 | B2 | 5/2018 | Nuta et al. |
| 9,993,292 | B2 | 6/2018 | Adams et al. |
| 10,039,561 | B2 | 8/2018 | Adams et al. |
| 10,076,384 | B2 | 9/2018 | Kasprzyk |
| 10,086,175 | B2 | 10/2018 | Torres et al. |
| 10,124,153 | B2 | 11/2018 | Feig |
| 10,136,829 | B2 | 11/2018 | Deno et al. |
| 10,149,690 | B2 | 12/2018 | Hawkins et al. |
| 10,159,505 | B2 | 12/2018 | Hakala et al. |
| 10,194,994 | B2 | 2/2019 | Deno et al. |
| 10,201,387 | B2 | 2/2019 | Grace et al. |
| 10,206,698 | B2 | 2/2019 | Hakala et al. |
| 10,226,265 | B2 | 3/2019 | Ku et al. |
| 10,245,410 | B2 | 4/2019 | Aggerholm |
| 10,327,846 | B1 | 6/2019 | Stark et al. |
| 10,328,290 | B2 | 6/2019 | Zhou et al. |
| 10,357,264 | B2 | 7/2019 | Kat-Kuoy |
| 10,405,923 | B2 | 9/2019 | Yu et al. |
| 10,406,031 | B2 | 9/2019 | Thyzel |
| 10,406,318 | B2 | 9/2019 | Williams |
| 10,420,569 | B2 | 9/2019 | Adams |
| 10,439,791 | B2 | 10/2019 | Kalhan |
| 10,441,300 | B2 | 10/2019 | Hawkins |
| 10,449,339 | B2 | 10/2019 | Wilson et al. |
| 10,463,430 | B2 | 11/2019 | Dick |
| 10,478,202 | B2 | 11/2019 | Adams et al. |
| 10,517,620 | B2 | 12/2019 | Adams |
| 10,517,621 | B1 | 12/2019 | Hakala et al. |
| 10,537,287 | B2 | 1/2020 | Braido et al. |
| 10,555,744 | B2 | 2/2020 | Nguyen et al. |
| 10,561,428 | B2 | 2/2020 | Eggert et al. |
| 10,583,277 | B2 | 3/2020 | Rundquist |
| 10,589,073 | B2 | 3/2020 | Mallaby |
| 10,617,850 | B2 | 4/2020 | Tal |
| 10,646,240 | B2 | 5/2020 | Betelia et al. |
| 10,668,245 | B2 | 6/2020 | Kanae |
| 10,682,178 | B2 | 6/2020 | Adams et al. |
| 10,695,531 | B2 | 6/2020 | Suzuki |
| 10,702,293 | B2 | 7/2020 | Adams et al. |
| 10,709,462 | B2 | 7/2020 | Nguyen et al. |
| 10,709,872 | B2 | 7/2020 | Alvarez et al. |
| 10,758,255 | B2 | 9/2020 | Adams |
| 10,797,684 | B1 | 10/2020 | Benz et al. |
| 10,799,688 | B2 | 10/2020 | Calhoun |
| 10,842,567 | B2 | 11/2020 | Grace et al. |
| 10,850,075 | B2 | 12/2020 | Tarunaga |
| 10,857,329 | B2 | 12/2020 | Davies |
| 10,864,355 | B2 | 12/2020 | Root et al. |
| 10,933,225 | B2 | 3/2021 | Campbell |
| 10,945,791 | B2 | 3/2021 | Verhagen et al. |
| 10,952,740 | B2 | 3/2021 | Dasnurkar et al. |
| 10,952,790 | B2 | 3/2021 | Haverkost et al. |
| 10,959,743 | B2 | 3/2021 | Adams et al. |
| 10,966,737 | B2 | 4/2021 | Nguyen |
| 10,967,156 | B2 | 4/2021 | Gulachenski |
| 10,973,538 | B2 | 4/2021 | Hakala et al. |
| 10,974,028 | B2 | 4/2021 | Buller et al. |
| 10,980,987 | B2 | 4/2021 | Tarunaga |
| 11,000,299 | B2 | 5/2021 | Hawkins et al. |

(56) References Cited

U.S. PATENT DOCUMENTS

| | | | |
|---|---|---|---|
| 11,020,135 | B1 | 6/2021 | Hawkins |
| 11,026,707 | B2 | 6/2021 | Ku et al. |
| 11,040,176 | B2 | 6/2021 | Blanchard et al. |
| 11,058,492 | B2 | 7/2021 | Grace et al. |
| 11,076,874 | B2 | 8/2021 | Hakala et al. |
| 11,116,939 | B2 | 9/2021 | Jamous et al. |
| 11,141,131 | B2 | 10/2021 | Stigall |
| 11,179,169 | B2 | 11/2021 | Brouillete et al. |
| 11,207,493 | B2 | 12/2021 | Suzuki et al. |
| 11,213,661 | B2 | 1/2022 | Spindler |
| 11,229,772 | B2 | 1/2022 | Nita |
| 11,229,776 | B2 | 1/2022 | Kugler et al. |
| 11,246,659 | B2 | 2/2022 | Grace et al. |
| 11,253,681 | B2 | 2/2022 | Williams |
| 11,266,817 | B2 | 3/2022 | Cope et al. |
| 11,389,171 | B2 | 7/2022 | Goldsmith |
| 11,389,628 | B2 | 7/2022 | Spencer |
| 11,395,669 | B2 | 7/2022 | O'Malley et al. |
| 11,399,862 | B2 | 8/2022 | Massimini et al. |
| 11,406,452 | B2 | 8/2022 | Efremkin |
| 11,406,799 | B2 | 8/2022 | McEvaddy et al. |
| 11,484,327 | B2 | 11/2022 | Anderson et al. |
| 11,540,848 | B2 | 1/2023 | Cai et al. |
| 11,564,729 | B2 | 1/2023 | Walzman |
| 11,602,363 | B2 | 3/2023 | Nguyen |
| 11,633,200 | B2 | 4/2023 | Anderson et al. |
| 11,672,585 | B2 | 6/2023 | Schultheis |
| 11,672,599 | B2 | 6/2023 | Schultheis et al. |
| 11,707,323 | B2 | 7/2023 | Schultheis et al. |
| 11,771,449 | B2 | 10/2023 | Adams et al. |
| 11,779,363 | B2 | 10/2023 | Vo |
| 11,826,530 | B2 | 11/2023 | Suzuki |
| 11,839,391 | B2 | 12/2023 | Schultheis et al. |
| 11,911,054 | B2 | 2/2024 | Singla |
| 11,911,056 | B2 | 2/2024 | Anderson et al. |
| 11,918,285 | B2 | 3/2024 | Sun et al. |
| 11,944,331 | B2 | 4/2024 | Anderson et al. |
| 11,950,793 | B2 | 4/2024 | Nguyen |
| 12,011,185 | B2 | 6/2024 | Vo |
| 12,023,098 | B2 | 7/2024 | Nguyen |
| 12,035,932 | B1 | 7/2024 | Nunes |
| 12,076,077 | B2 | 9/2024 | Mori |
| 12,144,516 | B2 | 11/2024 | Betelia |
| 12,178,458 | B1 | 12/2024 | Betelia et al. |
| 12,193,691 | B2 | 1/2025 | Adams |
| 2001/0016761 | A1 | 8/2001 | Rudie |
| 2001/0018569 | A1 | 8/2001 | Erbel |
| 2001/0020164 | A1 | 9/2001 | Papademetriou |
| 2001/0049464 | A1 | 12/2001 | Ganz |
| 2001/0051784 | A1 | 12/2001 | Brisken |
| 2002/0045811 | A1 | 4/2002 | Kittrell et al. |
| 2002/0052621 | A1 | 5/2002 | Fried et al. |
| 2002/0065512 | A1 | 5/2002 | Fjield et al. |
| 2002/0082553 | A1 | 6/2002 | Duchamp |
| 2002/0183620 | A1 | 12/2002 | Tearney |
| 2002/0183729 | A1 | 12/2002 | Farr et al. |
| 2002/0188204 | A1 | 12/2002 | McNamara et al. |
| 2003/0009157 | A1 | 1/2003 | Levine et al. |
| 2003/0050632 | A1 | 3/2003 | Fjield et al. |
| 2003/0065316 | A1 | 4/2003 | Levine et al. |
| 2003/0114901 | A1 | 6/2003 | Loeb et al. |
| 2003/0125719 | A1 | 7/2003 | Furnish |
| 2003/0144654 | A1* | 7/2003 | Hilal ................... A61B 18/042 606/34 |
| 2003/0176873 | A1 | 9/2003 | Chernenko et al. |
| 2004/0002677 | A1 | 1/2004 | Gentsler |
| 2004/0024349 | A1 | 2/2004 | Flock et al. |
| 2004/0073251 | A1 | 4/2004 | Weber |
| 2004/0097996 | A1 | 5/2004 | Rabiner |
| 2004/0133254 | A1 | 7/2004 | Sterzer et al. |
| 2004/0162508 | A1 | 8/2004 | Uebelacker |
| 2004/0210278 | A1* | 10/2004 | Boll ...................... A61B 18/24 607/89 |
| 2004/0243119 | A1 | 12/2004 | Lane et al. |
| 2004/0249401 | A1 | 12/2004 | Rabiner |
| 2004/0254570 | A1 | 12/2004 | Hadsjicostis |
| 2005/0010095 | A1 | 1/2005 | Stewart et al. |
| 2005/0021013 | A1 | 1/2005 | Visuri |
| 2005/0027337 | A1 | 2/2005 | Rudko et al. |
| 2005/0080396 | A1 | 4/2005 | Rontal |
| 2005/0113722 | A1 | 5/2005 | Schultheiss |
| 2005/0171437 | A1 | 8/2005 | Carberry |
| 2005/0171527 | A1 | 8/2005 | Bhola |
| 2005/0251131 | A1 | 11/2005 | Lesh |
| 2005/0259319 | A1 | 11/2005 | Brooker |
| 2005/0273014 | A1 | 12/2005 | Gianchandani et al. |
| 2005/0277839 | A1 | 12/2005 | Alderman et al. |
| 2006/0033241 | A1 | 2/2006 | Schewe et al. |
| 2006/0084966 | A1 | 4/2006 | Maguire et al. |
| 2006/0098921 | A1 | 5/2006 | Benaron et al. |
| 2006/0142703 | A1 | 6/2006 | Carter |
| 2006/0190022 | A1 | 8/2006 | Beyar et al. |
| 2006/0200039 | A1 | 9/2006 | Brockway et al. |
| 2006/0221528 | A1 | 10/2006 | Li et al. |
| 2006/0241524 | A1 | 10/2006 | Lee et al. |
| 2006/0241572 | A1 | 10/2006 | Zhou |
| 2006/0241733 | A1 | 10/2006 | Zhang et al. |
| 2006/0270976 | A1 | 11/2006 | Savage et al. |
| 2007/0027524 | A1 | 2/2007 | Johnson |
| 2007/0043340 | A1 | 2/2007 | Thyzel |
| 2007/0060990 | A1 | 3/2007 | Satake |
| 2007/0088380 | A1 | 4/2007 | Hirszowicz et al. |
| 2007/0118057 | A1 | 5/2007 | Ein-gal |
| 2007/0142779 | A1 | 6/2007 | Duane |
| 2007/0142819 | A1 | 6/2007 | El-Nounou et al. |
| 2007/0142821 | A1 | 6/2007 | Hennessy et al. |
| 2007/0142856 | A1 | 6/2007 | Jang |
| 2007/0179496 | A1 | 8/2007 | Swoyer |
| 2007/0239082 | A1 | 10/2007 | Schultheiss et al. |
| 2007/0255270 | A1 | 11/2007 | Carney |
| 2007/0264353 | A1 | 11/2007 | Myntti et al. |
| 2007/0270897 | A1 | 11/2007 | Skerven |
| 2007/0280311 | A1 | 12/2007 | Hofmann |
| 2007/0282301 | A1* | 12/2007 | Segalescu ......... A61M 25/1002 600/101 |
| 2007/0299392 | A1 | 12/2007 | Beyar et al. |
| 2008/0033519 | A1 | 2/2008 | Burwell |
| 2008/0081950 | A1 | 4/2008 | Koenig et al. |
| 2008/0086118 | A1 | 4/2008 | Lai |
| 2008/0095714 | A1 | 4/2008 | Castella et al. |
| 2008/0097251 | A1 | 4/2008 | Babaev |
| 2008/0108867 | A1 | 5/2008 | Zhou |
| 2008/0114341 | A1 | 5/2008 | Thyzel |
| 2008/0132810 | A1 | 6/2008 | Scoseria et al. |
| 2008/0175539 | A1* | 7/2008 | Brown ................... G02B 6/262 65/392 |
| 2008/0188843 | A1 | 8/2008 | Appling et al. |
| 2008/0195088 | A1 | 8/2008 | Farr et al. |
| 2008/0214891 | A1 | 9/2008 | Slenker et al. |
| 2008/0221550 | A1 | 9/2008 | Lee |
| 2008/0281157 | A1 | 11/2008 | Miyagi et al. |
| 2008/0296152 | A1 | 12/2008 | Voss |
| 2008/0319356 | A1 | 12/2008 | Cain et al. |
| 2009/0036803 | A1 | 2/2009 | Warlick et al. |
| 2009/0043300 | A1 | 2/2009 | Reitmajer et al. |
| 2009/0054881 | A1 | 2/2009 | Krespi |
| 2009/0097806 | A1 | 4/2009 | Viellerobe et al. |
| 2009/0125007 | A1 | 5/2009 | Splinter |
| 2009/0131921 | A1 | 5/2009 | Kurtz et al. |
| 2009/0192495 | A1 | 7/2009 | Ostrovsky et al. |
| 2009/0240242 | A1 | 9/2009 | Neuberger |
| 2009/0247945 | A1 | 10/2009 | Levit |
| 2009/0281531 | A1 | 11/2009 | Rizoiu |
| 2009/0292296 | A1 | 11/2009 | Pansky |
| 2009/0296751 | A1 | 12/2009 | Kewitsch et al. |
| 2009/0299327 | A1 | 12/2009 | Tilson et al. |
| 2009/0306533 | A1 | 12/2009 | Rousche |
| 2009/0312768 | A1 | 12/2009 | Hawkins et al. |
| 2010/0016862 | A1 | 1/2010 | Hawkins et al. |
| 2010/0036238 | A1 | 2/2010 | Neidert |
| 2010/0036294 | A1 | 2/2010 | Mantell et al. |
| 2010/0063491 | A1 | 3/2010 | Verhagen |
| 2010/0094209 | A1 | 4/2010 | Drasler et al. |
| 2010/0114020 | A1 | 5/2010 | Hawkins et al. |

(56) References Cited

U.S. PATENT DOCUMENTS

2010/0114065 A1 5/2010 Hawkins et al.
2010/0125268 A1 5/2010 Gustus et al.
2010/0160838 A1 6/2010 Krespi
2010/0160903 A1 6/2010 Krespi
2010/0168572 A1 7/2010 Sliwa
2010/0168836 A1 7/2010 Kassab
2010/0168862 A1 7/2010 Edie et al.
2010/0179632 A1 7/2010 Bruszewski et al.
2010/0191089 A1 7/2010 Stebler et al.
2010/0198114 A1 8/2010 Novak et al.
2010/0199773 A1 8/2010 Zhou
2010/0222786 A1 9/2010 Kassab
2010/0234875 A1 9/2010 Allex et al.
2010/0256535 A1 10/2010 Novak et al.
2010/0265733 A1* 10/2010 O'Leary .............. G02B 6/0006 362/555
2010/0286791 A1 11/2010 Goldsmith
2010/0316333 A1* 12/2010 Luther ................. G02B 6/3885 385/59
2011/0034832 A1 2/2011 Cioanta et al.
2011/0059415 A1 3/2011 Kasenbacher
2011/0082452 A1 4/2011 Melsky
2011/0082534 A1 4/2011 Wallace
2011/0118634 A1 5/2011 Golan
2011/0144502 A1 6/2011 Zhou et al.
2011/0184244 A1 7/2011 Kagaya et al.
2011/0208185 A1 8/2011 Diamant et al.
2011/0213349 A1 9/2011 Brown
2011/0245740 A1 10/2011 Novak et al.
2011/0257641 A1 10/2011 Hastings et al.
2011/0263921 A1 10/2011 Vrba et al.
2011/0275990 A1 11/2011 Besser et al.
2011/0306956 A1 12/2011 Islam
2012/0064141 A1 3/2012 Andreacchi et al.
2012/0071715 A1 3/2012 Beyar et al.
2012/0071867 A1 3/2012 Ryan
2012/0071889 A1 3/2012 Mantell et al.
2012/0089132 A1 4/2012 Dick et al.
2012/0095335 A1 4/2012 Sverdlik et al.
2012/0095461 A1 4/2012 Herscher et al.
2012/0116289 A1 5/2012 Hawkins et al.
2012/0116486 A1 5/2012 Naga et al.
2012/0123331 A1 5/2012 Satake
2012/0123399 A1 5/2012 Belikov
2012/0143131 A1* 6/2012 Tun ....................... A61M 25/10 604/101.02
2012/0157892 A1 6/2012 Reitmajer et al.
2012/0203255 A1 8/2012 Hawkins et al.
2012/0221013 A1 8/2012 Hawkins et al.
2012/0232409 A1 9/2012 Stahmann
2012/0238821 A1* 9/2012 Yoshida ............. A61B 1/00117 600/182
2012/0296367 A1 11/2012 Grovender et al.
2012/0323211 A1 12/2012 Ogle
2012/0330293 A1 12/2012 Arai
2013/0030431 A1 1/2013 Adams
2013/0030447 A1 1/2013 Adams
2013/0041355 A1 2/2013 Heeren et al.
2013/0046207 A1 2/2013 Capelli
2013/0046293 A1 2/2013 Arai et al.
2013/0053762 A1 2/2013 Rontal et al.
2013/0060234 A1 3/2013 Besser
2013/0110003 A1* 5/2013 Surti ........................ A61B 1/07 600/153
2013/0116714 A1 5/2013 Adams et al.
2013/0165764 A1 6/2013 Scheuermann
2013/0190803 A1 7/2013 Angel et al.
2013/0197614 A1 8/2013 Gustus
2013/0218054 A1 8/2013 Sverdlik et al.
2013/0226131 A1 8/2013 Bacino et al.
2013/0253466 A1 9/2013 Campbell
2013/0274726 A1 10/2013 Takayama
2013/0345617 A1 12/2013 Wallace
2014/0005576 A1 1/2014 Adams
2014/0005706 A1 1/2014 Gelfand et al.
2014/0012186 A1 1/2014 Thyzel
2014/0039002 A1 2/2014 Diodone et al.
2014/0039358 A1 2/2014 Zhou et al.
2014/0039513 A1 2/2014 Hakala
2014/0046229 A1 2/2014 Hawkins et al.
2014/0046353 A1 2/2014 Adams
2014/0052146 A1 2/2014 Curtis et al.
2014/0052147 A1 2/2014 Hakala et al.
2014/0058294 A1 2/2014 Gross et al.
2014/0074111 A1 3/2014 Hakala
2014/0114198 A1 4/2014 Samada et al.
2014/0128848 A1 5/2014 Appling et al.
2014/0153087 A1 6/2014 Hutchings et al.
2014/0155990 A1 6/2014 Nyuli
2014/0180069 A1 6/2014 Millett
2014/0180126 A1 6/2014 Millett
2014/0180134 A1 6/2014 Hoseit
2014/0188094 A1 7/2014 Islam
2014/0228829 A1 8/2014 Schmitt
2014/0257144 A1 9/2014 Capelli et al.
2014/0257148 A1 9/2014 Jie
2014/0276573 A1 9/2014 Miesel
2014/0288570 A1 9/2014 Adams
2014/0309536 A1 10/2014 Douk et al.
2014/0336626 A1 11/2014 Jiang
2014/0336637 A1 11/2014 Agrawal
2014/0357997 A1 12/2014 Hartmann
2015/0003900 A1 1/2015 Ullrich et al.
2015/0005576 A1 1/2015 Diodone et al.
2015/0039002 A1 2/2015 Hawkins
2015/0051499 A1* 2/2015 McGowan ......... A61B 5/02154 600/478
2015/0057648 A1 2/2015 Swift et al.
2015/0071591 A1 3/2015 Chen
2015/0073430 A1 3/2015 Hakala et al.
2015/0080875 A1 3/2015 Kasprzyk et al.
2015/0100048 A1 4/2015 Hiereth et al.
2015/0105715 A1 4/2015 Pikus et al.
2015/0119870 A1 4/2015 Rudie
2015/0126990 A1 5/2015 Sharma
2015/0141764 A1 5/2015 Harks et al.
2015/0250542 A1 9/2015 Islam
2015/0276689 A1 10/2015 Watanabe et al.
2015/0313732 A1 11/2015 Fulton, III
2015/0320432 A1 11/2015 Adams
2015/0342678 A1 12/2015 Deladurantaye et al.
2015/0342681 A1 12/2015 Lee
2015/0359432 A1 12/2015 Ehrenreich
2015/0359557 A1 12/2015 Shimokawa
2016/0008016 A1 1/2016 Cioanta et al.
2016/0016016 A1 1/2016 Taylor et al.
2016/0018602 A1 1/2016 Govari et al.
2016/0022294 A1 1/2016 Cioanta et al.
2016/0038087 A1 2/2016 Hunter
2016/0095610 A1 4/2016 Lipowski et al.
2016/0135828 A1 5/2016 Hawkins et al.
2016/0135891 A1 5/2016 Feldman
2016/0143522 A1 5/2016 Ransbury
2016/0151639 A1 6/2016 Scharf et al.
2016/0183819 A1 6/2016 Burnett
2016/0183957 A1 6/2016 Hakala et al.
2016/0184020 A1 6/2016 Kowalewski et al.
2016/0184022 A1 6/2016 Grace et al.
2016/0184023 A1 6/2016 Grace et al.
2016/0184526 A1 6/2016 Beyar
2016/0184570 A1 6/2016 Grace et al.
2016/0228187 A1 8/2016 Gross
2016/0234534 A1 8/2016 Kitahara et al.
2016/0262784 A1 9/2016 Grace et al.
2016/0270806 A1 9/2016 Wallace
2016/0302762 A1 10/2016 Stigall et al.
2016/0324564 A1 11/2016 Gerlach et al.
2016/0331389 A1 11/2016 Hakala et al.
2016/0339204 A1 11/2016 Williams
2016/0367274 A1 12/2016 Wallace
2016/0367275 A1 12/2016 Wallace
2017/0049463 A1 2/2017 Popovic et al.
2017/0056035 A1 3/2017 Adams

(56) References Cited

U.S. PATENT DOCUMENTS

| | | | |
|---|---|---|---|
| 2017/0086867 | A1 | 3/2017 | Adams |
| 2017/0119469 | A1 | 5/2017 | Shimizu et al. |
| 2017/0119470 | A1 | 5/2017 | Diamant et al. |
| 2017/0135709 | A1 | 5/2017 | Nguyen et al. |
| 2017/0151421 | A1 | 6/2017 | Asher |
| 2017/0192242 | A1 | 7/2017 | Laycock |
| 2017/0209050 | A1 | 7/2017 | Fengler et al. |
| 2017/0265942 | A1 | 9/2017 | Grace et al. |
| 2017/0303946 | A1 | 10/2017 | Ku et al. |
| 2017/0311965 | A1 | 11/2017 | Adams |
| 2018/0008348 | A1 | 1/2018 | Grace et al. |
| 2018/0042661 | A1 | 2/2018 | Long |
| 2018/0042677 | A1 | 2/2018 | Yu et al. |
| 2018/0045897 | A1* | 2/2018 | Chia .................... G02B 6/3855 |
| 2018/0049877 | A1 | 2/2018 | Venkatasubramanian |
| 2018/0085174 | A1 | 3/2018 | Radtke et al. |
| 2018/0092763 | A1 | 4/2018 | Dagan et al. |
| 2018/0095287 | A1 | 4/2018 | Jeng et al. |
| 2018/0098779 | A1 | 4/2018 | Betelia et al. |
| 2018/0152568 | A1 | 5/2018 | Thumpudi et al. |
| 2018/0169392 | A1 | 6/2018 | Franklin |
| 2018/0214677 | A1 | 8/2018 | Tarunaga |
| 2018/0238675 | A1 | 8/2018 | Wan |
| 2018/0256250 | A1 | 9/2018 | Adams et al. |
| 2018/0280005 | A1 | 10/2018 | Parmentier |
| 2018/0303501 | A1 | 10/2018 | Hawkins |
| 2018/0303503 | A1 | 10/2018 | Eggert et al. |
| 2018/0303504 | A1 | 10/2018 | Eggert et al. |
| 2018/0304053 | A1 | 10/2018 | Eggert et al. |
| 2018/0323571 | A1 | 11/2018 | Brown et al. |
| 2018/0333043 | A1 | 11/2018 | Teriluc |
| 2018/0360482 | A1 | 12/2018 | Nguyen |
| 2019/0029702 | A1 | 1/2019 | De Cicco |
| 2019/0029703 | A1 | 1/2019 | Wasdyke et al. |
| 2019/0069916 | A1 | 3/2019 | Hawkins et al. |
| 2019/0072378 | A1 | 3/2019 | Hane et al. |
| 2019/0097380 | A1 | 3/2019 | Luft et al. |
| 2019/0099588 | A1 | 4/2019 | Ramanath et al. |
| 2019/0104933 | A1 | 4/2019 | Stern |
| 2019/0117242 | A1 | 4/2019 | Lawinger |
| 2019/0150960 | A1 | 5/2019 | Nguyen et al. |
| 2019/0150961 | A1 | 5/2019 | Tozzi |
| 2019/0159792 | A1 | 5/2019 | Panian |
| 2019/0167349 | A1 | 6/2019 | Shamay |
| 2019/0175111 | A1 | 6/2019 | Genereux et al. |
| 2019/0175300 | A1 | 6/2019 | Horn et al. |
| 2019/0175372 | A1 | 6/2019 | Boyden et al. |
| 2019/0175407 | A1 | 6/2019 | Bacher |
| 2019/0209368 | A1 | 7/2019 | Park et al. |
| 2019/0232066 | A1 | 8/2019 | Lim et al. |
| 2019/0247680 | A1 | 8/2019 | Mayer |
| 2019/0262594 | A1 | 8/2019 | Ogata et al. |
| 2019/0265419 | A1 | 8/2019 | Tayebati |
| 2019/0282249 | A1 | 9/2019 | Tran et al. |
| 2019/0282250 | A1 | 9/2019 | Tran et al. |
| 2019/0285803 | A1* | 9/2019 | Van Zuylen ........... G02B 6/245 |
| 2019/0321100 | A1 | 10/2019 | Masotti et al. |
| 2019/0321101 | A1 | 10/2019 | Massoti et al. |
| 2019/0328259 | A1 | 10/2019 | Deno et al. |
| 2019/0365400 | A1 | 12/2019 | Adams et al. |
| 2019/0380589 | A1 | 12/2019 | Lloret |
| 2019/0388002 | A1 | 12/2019 | Bozsak et al. |
| 2019/0388110 | A1 | 12/2019 | Nguyen et al. |
| 2019/0388133 | A1 | 12/2019 | Sharma |
| 2019/0388151 | A1 | 12/2019 | Bhawalkar |
| 2019/0388654 | A1 | 12/2019 | Chou |
| 2020/0000484 | A1 | 1/2020 | Hawkins |
| 2020/0008856 | A1 | 1/2020 | Harmouche |
| 2020/0022754 | A1 | 1/2020 | Cottone |
| 2020/0038087 | A1 | 2/2020 | Harmouche |
| 2020/0046429 | A1 | 2/2020 | Tschida et al. |
| 2020/0046949 | A1 | 2/2020 | Chisena et al. |
| 2020/0054352 | A1 | 2/2020 | Brouillette et al. |
| 2020/0060814 | A1 | 2/2020 | Murphy |
| 2020/0061931 | A1 | 2/2020 | Brown et al. |
| 2020/0069371 | A1 | 3/2020 | Brown et al. |
| 2020/0085458 | A1 | 3/2020 | Nguyen et al. |
| 2020/0085459 | A1 | 3/2020 | Adams |
| 2020/0101269 | A1 | 4/2020 | Hayes |
| 2020/0107960 | A1 | 4/2020 | Bacher |
| 2020/0108236 | A1 | 4/2020 | Salazar et al. |
| 2020/0129195 | A1 | 4/2020 | McGowan et al. |
| 2020/0129741 | A1 | 4/2020 | Kawwas |
| 2020/0155812 | A1 | 5/2020 | Zhang et al. |
| 2020/0197019 | A1 | 6/2020 | Harper |
| 2020/0205890 | A1 | 7/2020 | Harlev |
| 2020/0246032 | A1 | 8/2020 | Betelia et al. |
| 2020/0289202 | A1 | 9/2020 | Miyagawa et al. |
| 2020/0297366 | A1 | 9/2020 | Nguyen et al. |
| 2020/0337717 | A1 | 10/2020 | Walzman |
| 2020/0345380 | A1 | 11/2020 | Boyle et al. |
| 2020/0383724 | A1 | 12/2020 | Adams et al. |
| 2020/0397230 | A1 | 12/2020 | Massimini et al. |
| 2020/0397453 | A1 | 12/2020 | McGowan |
| 2020/0398033 | A1 | 12/2020 | McGowan et al. |
| 2020/0405333 | A1 | 12/2020 | Massimini et al. |
| 2020/0405391 | A1 | 12/2020 | Massimini |
| 2020/0406009 | A1 | 12/2020 | Massimini |
| 2020/0406010 | A1 | 12/2020 | Massimini et al. |
| 2021/0038237 | A1 | 2/2021 | Adams |
| 2021/0085347 | A1 | 3/2021 | Phan et al. |
| 2021/0085348 | A1 | 3/2021 | Nguyen |
| 2021/0085383 | A1 | 3/2021 | Vo et al. |
| 2021/0085395 | A1 | 3/2021 | Iwama |
| 2021/0116302 | A1 | 4/2021 | Jean-Ruel |
| 2021/0128241 | A1 | 5/2021 | Schultheis |
| 2021/0137598 | A1 | 5/2021 | Cook et al. |
| 2021/0153939 | A1 | 5/2021 | Cook |
| 2021/0177442 | A1 | 6/2021 | Girdhar et al. |
| 2021/0177445 | A1 | 6/2021 | Nguyen |
| 2021/0186613 | A1 | 6/2021 | Cook |
| 2021/0212765 | A1 | 7/2021 | Verhagen |
| 2021/0220052 | A1 | 7/2021 | Cook |
| 2021/0220053 | A1 | 7/2021 | Cook |
| 2021/0244473 | A1 | 8/2021 | Cook et al. |
| 2021/0267685 | A1 | 9/2021 | Schultheis |
| 2021/0275247 | A1 | 9/2021 | Schultheis |
| 2021/0275249 | A1 | 9/2021 | Massimini et al. |
| 2021/0282792 | A1 | 9/2021 | Adams et al. |
| 2021/0290259 | A1 | 9/2021 | Hakala et al. |
| 2021/0290286 | A1 | 9/2021 | Cook |
| 2021/0290305 | A1 | 9/2021 | Cook |
| 2021/0298603 | A1 | 9/2021 | Feldman |
| 2021/0338258 | A1 | 11/2021 | Hawkins et al. |
| 2021/0353359 | A1 | 11/2021 | Cook |
| 2021/0369348 | A1 | 12/2021 | Cook |
| 2021/0378743 | A1 | 12/2021 | Massimini et al. |
| 2021/0378744 | A1 | 12/2021 | Fanier et al. |
| 2021/0386479 | A1 | 12/2021 | Massimini et al. |
| 2022/0000505 | A1 | 1/2022 | Hauser |
| 2022/0000506 | A1 | 1/2022 | Hauser |
| 2022/0000507 | A1 | 1/2022 | Hauser |
| 2022/0000508 | A1 | 1/2022 | Schmitt et al. |
| 2022/0000509 | A1 | 1/2022 | Laser et al. |
| 2022/0000551 | A1 | 1/2022 | Govari et al. |
| 2022/0001138 | A1 | 1/2022 | Howell |
| 2022/0008130 | A1 | 1/2022 | Massimini et al. |
| 2022/0008693 | A1 | 1/2022 | Humbert et al. |
| 2022/0015785 | A1 | 1/2022 | Hakala et al. |
| 2022/0021190 | A1 | 1/2022 | Pecquois |
| 2022/0022902 | A1 | 1/2022 | Spano |
| 2022/0022912 | A1 | 1/2022 | Efremkin |
| 2022/0023528 | A1 | 1/2022 | Long et al. |
| 2022/0040454 | A1 | 2/2022 | Hamm |
| 2022/0054194 | A1 | 2/2022 | Bacher et al. |
| 2022/0071704 | A1 | 3/2022 | Le |
| 2022/0168594 | A1 | 6/2022 | Mayer |
| 2022/0183738 | A1 | 6/2022 | Flores et al. |
| 2022/0218402 | A1 | 7/2022 | Schultheis |
| 2022/0249165 | A1 | 8/2022 | Cook |
| 2022/0249166 | A1 | 8/2022 | Cook et al. |
| 2022/0273324 | A1 | 9/2022 | Schultheis |
| 2022/0287732 | A1 | 9/2022 | Anderson et al. |
| 2022/0313293 | A1 | 10/2022 | Singh |

(56) References Cited

U.S. PATENT DOCUMENTS

| | | | |
|---|---|---|---|
| 2022/0313359 | A1 | 10/2022 | Schultheis et al. |
| 2022/0338890 | A1 | 10/2022 | Anderson et al. |
| 2022/0354578 | A1 | 11/2022 | Cook |
| 2022/0387106 | A1 | 12/2022 | Cook |
| 2023/0013920 | A1 | 1/2023 | Massimini |
| 2023/0064371 | A1 | 3/2023 | Cook et al. |
| 2023/0137107 | A1 | 5/2023 | Cook et al. |
| 2023/0157754 | A1 | 5/2023 | Bacher et al. |
| 2023/0200906 | A1 | 6/2023 | Cook et al. |
| 2023/0233256 | A1 | 7/2023 | Cook et al. |
| 2023/0240748 | A1 | 8/2023 | Cook et al. |
| 2023/0248376 | A1 | 8/2023 | Anderson et al. |
| 2023/0255635 | A1 | 8/2023 | Schultheis et al. |
| 2023/0255688 | A1 | 8/2023 | Schultheis et al. |
| 2023/0255689 | A1 | 8/2023 | Schultheis et al. |
| 2023/0310054 | A1 | 10/2023 | Schultheis |
| 2023/0310067 | A1 | 10/2023 | Schultheis et al. |
| 2023/0310073 | A1 | 10/2023 | Adams et al. |
| 2023/0320576 | A1 | 10/2023 | Feldman |
| 2023/0338088 | A1 | 10/2023 | Massimini et al. |
| 2023/0338089 | A1 | 10/2023 | Schultheis |
| 2023/0414234 | A1 | 12/2023 | Anderson et al. |
| 2024/0001076 | A1 | 1/2024 | Gelsinger |
| 2024/0016508 | A1 | 1/2024 | Kocur |
| 2024/0016544 | A1 | 1/2024 | Schultheis et al. |
| 2024/0016545 | A1 | 1/2024 | Schultheis et al. |
| 2024/0023813 | A1 | 1/2024 | Milner |
| 2024/0032995 | A1 | 2/2024 | Schultheis et al. |
| 2024/0033002 | A1 | 2/2024 | Cook |
| 2024/0041520 | A1 | 2/2024 | Schultheis et al. |
| 2024/0050170 | A1 | 2/2024 | Fournier |
| 2024/0050696 | A1 | 2/2024 | Japuntich |
| 2024/0058060 | A1 | 2/2024 | Cook |
| 2024/0065711 | A1 | 2/2024 | Hendrickson |
| 2024/0065712 | A1 | 2/2024 | Schultheis |
| 2024/0099773 | A1 | 3/2024 | Schabert |
| 2024/0122648 | A1 | 4/2024 | Cook |
| 2024/0165658 | A1 | 5/2024 | Fu |
| 2024/0173044 | A1 | 5/2024 | Chen et al. |
| 2024/0173526 | A1 | 5/2024 | Kofidis |
| 2024/0189543 | A1 | 6/2024 | Salinas |
| 2024/0216062 | A1 | 7/2024 | Cook |
| 2024/0260981 | A1 | 8/2024 | Betelia |
| 2024/0260982 | A1 | 8/2024 | Peterson |
| 2024/0277410 | A1 | 8/2024 | Cook |
| 2024/0277974 | A1 | 8/2024 | Oehler |
| 2024/0277980 | A1 | 8/2024 | O'Neill |
| 2024/0285296 | A1 | 8/2024 | Vo |
| 2024/0285922 | A1 | 8/2024 | Chu |
| 2024/0299051 | A1 | 9/2024 | Sidhu et al. |
| 2024/0307119 | A1 | 9/2024 | Nguyen |
| 2024/0325045 | A1 | 10/2024 | Otake |
| 2024/0382258 | A1 | 11/2024 | Schultheis |
| 2025/0025237 | A1 | 1/2025 | Cook |
| 2025/0040947 | A1 | 2/2025 | Schultheis |

FOREIGN PATENT DOCUMENTS

| | | | |
|---|---|---|---|
| AU | 2022227829 | | 9/2022 |
| CA | 2229806 | | 3/1997 |
| CA | 2281519 | | 8/1998 |
| CA | 2983655 | | 10/2016 |
| CA | 3209797 | | 9/2022 |
| CN | 102057422 | | 5/2011 |
| CN | 107072666 | A | 8/2017 |
| CN | 109223100 | | 1/2019 |
| CN | 110638501 | | 1/2020 |
| CN | 110638501 | A | 1/2020 |
| CN | 106794043 | | 3/2020 |
| CN | 107411805 | | 1/2022 |
| CN | 107899126 | | 1/2022 |
| CN | 109475378 | | 1/2022 |
| CN | 113876388 | | 1/2022 |
| CN | 113877044 | | 1/2022 |
| CN | 113907838 | | 1/2022 |
| CN | 113951972 | A | 1/2022 |
| CN | 113951973 | A | 1/2022 |
| CN | 113974765 | | 1/2022 |
| CN | 113974826 | A | 1/2022 |
| CN | 113993463 | | 1/2022 |
| CN | 215384399 | | 1/2022 |
| CN | 215386905 | | 1/2022 |
| CN | 215458400 | | 1/2022 |
| CN | 215458401 | | 1/2022 |
| CN | 215505065 | | 1/2022 |
| CN | 215534803 | | 1/2022 |
| CN | 215537694 | | 1/2022 |
| CN | 215584286 | | 1/2022 |
| CN | 215606068 | | 1/2022 |
| CN | 215651393 | | 1/2022 |
| CN | 215651394 | | 1/2022 |
| CN | 215651484 | | 1/2022 |
| CN | 215653328 | | 1/2022 |
| CN | 114053552 | | 2/2022 |
| CN | 115175625 | | 10/2022 |
| CN | 117752412 | | 3/2024 |
| CN | 118055734 | | 5/2024 |
| DE | 3038445 | A1 | 5/1982 |
| DE | 3836337 | A1 | 4/1990 |
| DE | 3913027 | A1 | 10/1990 |
| DE | 69431758 | | 1/2003 |
| DE | 10230626 | | 1/2004 |
| DE | 202008016760 | | 3/2009 |
| DE | 102007046902 | | 4/2009 |
| DE | 102008034702 | | 1/2010 |
| DE | 102009007129 | | 8/2010 |
| DE | 202010009899 | | 11/2010 |
| DE | 102013201928 | | 8/2014 |
| DE | 102020117713 | | 1/2022 |
| EP | 0119296 | | 9/1984 |
| EP | 0261831 | B1 | 6/1992 |
| EP | 558297 | A2 | 9/1993 |
| EP | 0571306 | A1 | 11/1993 |
| EP | 0547146 | | 7/1995 |
| EP | 1179993 | A1 | 2/2002 |
| EP | 1946712 | | 7/2008 |
| EP | 1946712 | A1 | 7/2008 |
| EP | 1453566 | | 9/2008 |
| EP | 2157569 | | 2/2010 |
| EP | 2470248 | | 7/2012 |
| EP | 2879595 | | 6/2015 |
| EP | 2879595 | A1 | 6/2015 |
| EP | 2944264 | A1 | 6/2015 |
| EP | 3226795 | A1 | 10/2017 |
| EP | 3266487 | | 1/2018 |
| EP | 3318204 | | 5/2018 |
| EP | 2879607 | | 2/2019 |
| EP | 3461438 | A1 | 4/2019 |
| EP | 3473195 | A1 | 4/2019 |
| EP | 2961463 | | 5/2019 |
| EP | 3240603 | | 5/2019 |
| EP | 3197381 | | 3/2020 |
| EP | 3643260 | A1 | 4/2020 |
| EP | 3240494 | | 3/2021 |
| EP | 3522812 | | 12/2021 |
| EP | 3076881 | B1 | 1/2022 |
| EP | 3932342 | | 1/2022 |
| EP | 3936140 | | 1/2022 |
| EP | 3960099 | | 3/2022 |
| EP | 4051154 | | 9/2022 |
| EP | 4129213 | | 2/2023 |
| EP | 4277537 | | 11/2023 |
| EP | 4297669 | | 1/2024 |
| EP | 4146322 | | 4/2024 |
| EP | 3182931 | | 6/2024 |
| EP | 3950036 | | 8/2024 |
| EP | 4034005 | | 12/2024 |
| GB | 1082397 | | 9/1967 |
| JP | S62275446 | A | 11/1987 |
| JP | H05264763 | | 10/1993 |
| JP | 1996089511 | | 4/1996 |
| JP | H09117407 | | 5/1997 |
| JP | 2001520070 | | 10/2001 |
| JP | 2004519296 | | 7/2004 |

(56) References Cited

FOREIGN PATENT DOCUMENTS

| | | | | | |
|---|---|---|---|---|---|
| JP | 2008506447 | | | 3/2008 | |
| JP | 2008083273 | | | 4/2008 | |
| JP | 2008083273 | A | * | 4/2008 | |
| JP | 2009519777 | | | 5/2009 | |
| JP | 2009213589 | | | 9/2009 | |
| JP | 2011524203 | | | 9/2011 | |
| JP | 4805208 | | | 11/2011 | |
| JP | 4808620 | | | 11/2011 | |
| JP | 2012505050 | | | 3/2012 | |
| JP | 2014123147 | | | 7/2014 | |
| JP | 2014123147 | A | * | 7/2014 | ......... A61B 1/00117 |
| JP | A2014516614 | | | 7/2014 | |
| JP | A2015522344 | | | 8/2015 | |
| JP | 2015217215 | | | 12/2015 | |
| JP | 2018538077 | | | 12/2018 | |
| JP | 2019521747 | A | | 8/2019 | |
| JP | 2024511710 | | | 3/2024 | |
| KR | 20050098932 | | | 10/2005 | |
| KR | 20080040111 | | | 5/2008 | |
| KR | 20160090877 | A | | 8/2016 | |
| KR | 20180054041 | | | 5/2018 | |
| KR | 20180054041 | A | * | 5/2018 | |
| WO | WO9007904 | A1 | | 7/1990 | |
| WO | WO9105332 | A1 | | 4/1991 | |
| WO | 9203095 | A1 | | 3/1992 | |
| WO | WO9208515 | | | 5/1992 | |
| WO | WO9524867 | | | 9/1995 | |
| WO | 1999002095 | A1 | | 1/1999 | |
| WO | 1999020189 | A1 | | 4/1999 | |
| WO | WO200067648 | | | 11/2000 | |
| WO | WO2000067648 | A1 | | 11/2000 | |
| WO | WO0103599 | | | 1/2001 | |
| WO | WO0103599 | A2 | | 1/2001 | |
| WO | 20060006169 | A2 | | 1/2006 | |
| WO | WO2006006169 | | | 1/2006 | |
| WO | WO2009121017 | | | 10/2009 | |
| WO | WO2009149321 | A1 | | 12/2009 | |
| WO | WO2009152352 | A2 | | 12/2009 | |
| WO | 2010042653 | A1 | | 4/2010 | |
| WO | WO2011094379 | | | 8/2011 | |
| WO | 20110126580 | A2 | | 10/2011 | |
| WO | WO2011126580 | A3 | | 10/2011 | |
| WO | WO2012025833 | | | 3/2012 | |
| WO | WO2012042619 | | | 4/2012 | |
| WO | WO20120052924 | A1 | | 4/2012 | |
| WO | WO2012058156 | | | 5/2012 | |
| WO | WO20120120495 | A2 | | 9/2012 | |
| WO | WO2013119662 | | | 8/2013 | |
| WO | 20130169807 | A1 | | 11/2013 | |
| WO | WO2013169807 | | | 11/2013 | |
| WO | WO2014025397 | A1 | | 2/2014 | |
| WO | WO20140022867 | A1 | | 2/2014 | |
| WO | WO2014138582 | | | 9/2014 | |
| WO | WO2015056662 | | | 4/2015 | |
| WO | WO2015097251 | A2 | | 7/2015 | |
| WO | 20150177790 | A1 | | 11/2015 | |
| WO | WO2016014999 | | | 1/2016 | |
| WO | WO2016089683 | A1 | | 6/2016 | |
| WO | WO2016090175 | | | 6/2016 | |
| WO | WO2016098670 | | | 6/2016 | |
| WO | WO2016109739 | | | 7/2016 | |
| WO | WO2016143556 | | | 9/2016 | |
| WO | WO2016151595 | A1 | | 9/2016 | |
| WO | WO20170192869 | A1 | | 11/2017 | |
| WO | 20180022641 | A1 | | 2/2018 | |
| WO | WO2018022593 | A1 | | 2/2018 | |
| WO | WO2018083666 | | | 5/2018 | |
| WO | 20180175322 | A1 | | 9/2018 | |
| WO | WO2018175322 | | | 9/2018 | |
| WO | WO2018191013 | | | 10/2018 | |
| WO | WO2019200201 | A1 | | 10/2019 | |
| WO | WO2019222843 | | | 11/2019 | |
| WO | WO2019240064 | A1 | | 12/2019 | |
| WO | WO2020056031 | | | 3/2020 | |
| WO | WO20200086361 | A1 | | 4/2020 | |
| WO | WO2020089876 | A1 | | 5/2020 | |
| WO | WO2020157648 | | | 8/2020 | |
| WO | WO2020256898 | | | 12/2020 | |
| WO | WO2020256898 | A1 | | 12/2020 | |
| WO | WO2020256949 | | | 12/2020 | |
| WO | WO2020256949 | A1 | | 12/2020 | |
| WO | WO2020263469 | A1 | | 12/2020 | |
| WO | WO2020263685 | A1 | | 12/2020 | |
| WO | WO2020263687 | A1 | | 12/2020 | |
| WO | WO2020263688 | A1 | | 12/2020 | |
| WO | WO2020263689 | A1 | | 12/2020 | |
| WO | WO2021061451 | | | 4/2021 | |
| WO | WO2021067563 | | | 4/2021 | |
| WO | WO2021086571 | A1 | | 5/2021 | |
| WO | WO2021096922 | A1 | | 5/2021 | |
| WO | WO2021101766 | | | 5/2021 | |
| WO | WO2021101766 | A1 | | 5/2021 | |
| WO | WO2021126762 | A1 | | 6/2021 | |
| WO | WO2021150502 | A1 | | 7/2021 | |
| WO | WO2021162855 | A1 | | 8/2021 | |
| WO | WO2021173417 | A1 | | 9/2021 | |
| WO | WO2021183367 | A1 | | 9/2021 | |
| WO | WO2021183401 | A1 | | 9/2021 | |
| WO | WO2021188233 | A1 | | 9/2021 | |
| WO | WO2021231178 | A1 | | 11/2021 | |
| WO | WO2021247685 | A1 | | 12/2021 | |
| WO | WO2021257425 | A1 | | 12/2021 | |
| WO | WO2022007490 | | | 1/2022 | |
| WO | WO2022008440 | | | 1/2022 | |
| WO | WO2022010767 | A1 | | 1/2022 | |
| WO | WO2022055784 | | | 3/2022 | |
| WO | WO2022125525 | | | 6/2022 | |
| WO | WO2022154954 | | | 7/2022 | |
| WO | WO2022173719 | | | 8/2022 | |
| WO | WO2022183075 | | | 9/2022 | |
| WO | WO2022187058 | | | 9/2022 | |
| WO | WO2022216488 | | | 10/2022 | |
| WO | WO2022240674 | | | 11/2022 | |
| WO | WO2022260932 | | | 12/2022 | |
| WO | WO2023107334 | | | 6/2023 | |
| WO | WO2024079108 | | | 4/2024 | |
| WO | WO2024107418 | | | 5/2024 | |

OTHER PUBLICATIONS

Stelzle, F., et al. Tissue Discrimination by Uncorrected Autofluorescence Spectra: A Proof-of-Principle Study for Tissue-Specific Laser Surgery, Sensors, 2013, pp. 13717-13731, vol. 13, Basel, Switzerland.
Tagawa, Y., et al. "Structure of laser-induced shock wave in water", Japan Society for the Promotion of Science, 2016.
Shen, Y., et al. "Theoretical and experimental studies of directivity of sound field generated by pulsed laser induced breakdown in liquid water", SPIE, 2013, pp. 8796141-8796148, vol. 8796, SPIE.
Preisack, M., et al. "Ultrafast imaging of tissue ablation by a XeCl excimer laser in saline", Lasers in Surgery and Medicine, 1992, pp. 520-527, vol. 12, Wiley-Liss Inc.
Versluis, M., et al. "How Snapping Shrimp Snap: Through Cavitating Bubbles", Science Mag, 2000, pp. 2114-2117, vol. 289, American Association for the Advancement of Science, Washington DC, USA.
Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.
Zhang, Q., et al. "Improved Instruments and Methods for the Photographic Study of Spark-Induced Cavitation Bubbles", Water, 2018, pp. 1-12, vol. 10, No. 1683.
"Damage threshold of fiber facets", NKT Photonics, 2012, pp. 1-4, Denmark.
Smith, A., et al. "Bulk and surface laser damage of silica by picosecond and nanosecond pulses at 1064 nm", Applied Optics, 2008, pp. 4812-4832, vol. 47, No. 26, Optical Society of America.
Smith, A., et al. "Deterministic Nanosecond Laser-Induced Breakdown Thresholds In Pure and Yb3 Doped Fused Silica", SPIE, 2007, pp. 6453171-64531712, vol. 6453, SPIE.

(56) References Cited

OTHER PUBLICATIONS

Sun, X., et al. "Laser Induced Damage to Large Core Optical Fiber by High Peak Power Laser", Specialty Photonics Division, 2010.
Smith, A., et al. "Nanosecond laser-induced breakdown in pure and Yb3 doped fused silica", SPIE, 2007, vol. 6403, SPIE.
Smith, A., et al. "Optical Damage Limits to Pulse Energy From Fibers", IEEE Journal of Selected Topics in Quantum Electronics, 2009, pp. 153-158, vol. 15, No. 1, IEEE.
Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.
Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.
Reichel, E., et al. "Laser-induced Shock Wave Lithotripsy with a Regenerative Energy Converter", Lasers in Medical Science, 1992, pp. 423-425, vol. 7, Bailliere Tindall.
Hardy, L., et al. "Cavitation Bubble Dynamics during Thulium Fiber Laser Lithotripsy", SPIE BiOS, 2016, vol. 9689, SPIE.
Deckelbaum, L., "Coronary Laser Angioplasty", Lasers in Surgery and Medicine, 1994, pp. 101-110, vol. 14, Wiley-Liss Inc., Conneticuit, USA.
Shangguan, H., et al. "Effects of Material Properties on Laser-induced Bubble Formation in Absorbing Liquids and On Submerged Targets", Diagnostic and Therapeutic Cardiovascular Interventions VII, SPIE, 1997, pp. 783-791, vol. 2869, SPIE.
Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.
Vogel, A., et al. "Minimization of Cavitation Effects in Pulsed Laser Ablation Illustrated on Laser Angioplasty", Applied Physics, 1996, pp. 173-182, vol. 62, Springer-Verlag.
Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.
Varghese, B., et al. "Influence of absorption induced thermal initiation pathway on irradiance threshold for laser Induced breakdown", Biomedical Optics Express, 2015, vol. 6, No. 4, Optical Society of America.
Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.
International Search Report and Written Opinion dated Jun. 27, 2018, in PCT Application Serial No. PCT/US2018/027121.
International Search Report and Written Opinion dated Jul. 20, 2018, in PCT Application Serial No. PCT/US2018/027801.
International Search Report and Written Opinion dated Jul. 20, 2018, in PCT Application Serial No. PCT/US2018/027784.
European Search Report, for European Patent Application No. 18185152, mailed Dec. 13, 2018.
International Search Report and Written Opinion dated May 22, 2019, in PCT Application Serial No. PCT/US2019/022009.
International Search Report and Written Opinion dated May 29, 2019, in PCT Application Serial No. PCT/US2019/022016.
International Search Report and Written Opinion dated Jun. 22, 2018, in Application Serial No. NL2019807, issued by the European Patent Office.
Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26, Wiley-Liss Inc.
Chen, Sung-Liang, "Review of Laser-Generated Ultrasound Transmitters and their Applications to All-Optical Ultrasound Transducers and Imaging", Appl. Sci. 2017, 7, 25.
Colchester, R., et al. "Laser-Generated ultrasound with optica fibres using functionalised carbon nanotube composite coatings", Appl. Phys. Lett., 2014, vol. 104, 173504, American Institute of Physics.
Poduval, R., et al. "Optical fiber ultrasound transmitter with electrospun carbon nanotube-polymer composite", Appl. Phys. Lett., 2017, vol. 110, 223701, American Institute of Physics.
Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.
Kim, J., et al. "Optical Fiber Laser-Generated-Focused-Ultrasound Transducers for Intravascular Therapies", IEEE, 2017.
Kang, H., et al. "Enhanced photocoagulation with catheter-based diffusing optical device", Journal of Biomedical Optics, 2012, vol. 17, Issue 11, 118001, SPIE.
International Search Report and Written Opinion dated Jan. 3, 2020, in PCT Application Serial No. PCT/US2019/056579.
Communication Pursuant to Article 94(3) EPC, for European Patent Application No. 18185152.8, mailed Jan. 16, 2019.
European Search Report, for European Patent Application No. 18185152.8, mailed Dec. 20, 2018.
International Search Report and Written Opinion dated Jul. 29, 2020 in PCT Application Serial No. PCT/US2020/034005.
International Search Report and Written Opinion dated Sep. 11, 2020 in PCT Application Serial No. PCT/US2020/038517.
International Search Report and Written Opinion dated Sep. 9, 2020 in PCT Application Serial No. PCT/US2020/038530.
International Search Report and Written Opinion dated Sep. 11, 2020 in PCT Application Serial No. PCT/US2020/038521.
International Search Report and Written Opinion dated Sep. 7, 2020 in PCT Application Serial No. PCT/US2020/034642.
International Preliminary Report on Patentability dated Sep. 15, 2020 in PCT Application Serial No. PCT/US2019/022009.
International Search Report and Written Opinion dated Sep. 14, 2020 in PCT Application Serial No. PCT/US2020/038523.
International Search Report and Written Opinion dated Oct. 2, 2020 in PCT Application Serial No. PCT/US2020/036107.
Schafter+Kirchhoff, Laser Beam Couplers series 60SMS for coupling into single-mode and polarization-maintaining fiber cables, Schafter+Kirchhoff, pp. 1-5, Germany.
International Search Report and Written Opinion dated Jan. 29, 2020 in PCT Application Serial No. PCT/US2020/059961.
International Search Report and Written Opinion dated Jan. 20, 2020 in PCT Application Serial No. PCT/US2020/054792.
Partial Search Report and Provisional Opinion dated Feb. 19, 2021 in PCT Application Serial No. PCT/US2020/059960.
Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.
Nademanee, Koonlawee, et al. "A new approach for catheter ablation of atrial fibrillation: mapping of the electrophysiologic substrate." Journal of the American College of Cardiology 43.11 (2004): 2044-2053.
Calkins, Hugh. "Three dimensional mapping of atrial fibrillation: techniques and necessity." Journal of interventional cardiac electrophysiology 13.1 (2005): 53-59.
Shariat, Mohammad Hassan. Processing the intracardiac electrogram for atrial fibrillation ablation. Diss. Queen's University (Canada), 2016.
Meng et al., "Accurate Recovery Of Atrial Endocardial Potential Maps From Non-contact Electrode Data." Auckland Bioengineering Institute. (ID 1421).
Jiang et al., "Multielectrode Catheter For Substrate Mapping For Scar-related VT Ablation: A Comparison Between Grid Versus Linear Configurations." UChicago Medicine, Center for Arrhythmia Care, Chicago IL (ID 1368).
Sacher et al., "Comparison Of Manual Vs Automatic Annotation To Identify Abnormal Substrate For Scar Related VT Ablation." LIRYC Institute, Bordeaux University Hospital, France (ID 1336).
Oriel Instruments, "Introduction to Beam Splitters for Optical Research Applications", Apr. 2014, pp. 1-9, https://www.azoptics.com/Article.aspx?ArticaID=871.

(56) References Cited

OTHER PUBLICATIONS

International Search Report and Written Opinion dated Apr. 12, 2021 in PCT Application Serial No. PCT/US2020/059960.
International Search Report and Written Opinion dated Apr. 13, 2021 in PCT Application Serial No. PCT/US2020/064846.
International Search Report and Written Opinion dated Apr. 13, 2021 in PCT Application Serial No. PCT/US2021/013944.
International Search Report and Written Opinion dated May 25, 2021 in PCT Application Serial No. PCT/US2021/017604.
International Search Report and Written Opinion dated Jun. 2, 2021 in PCT Application Serial No. PCT/US2021/018522.
International Search Report and Written Opinion dated Jun. 2, 2021 in PCT Application Serial No. PCT/US2021/015204.
International Search Report and Written Opinion dated Jun. 17, 2021 in PCT Application Serial No. PCT/US2021/020934.
International Search Report and Written Opinion dated Jul. 13, 2021 in PCT Application Serial No. PCT/US2021/024216.
International Search Report and Written Opinion dated Jun. 22, 2021 in PCT Application Serial No. PCT/US2021/020937.
International Search Report and Written Opinion dated Jun. 24, 2021 in PCT Application Serial No. PCT/US2021/021272.
International Search Report and Written Opinion dated Aug. 20, 2021 in PCT Application Serial No. PCT/US2021/031130.
International Search Report and Written Opinion dated Nov. 8, 2022 in PCT Application Serial No. PCTUS/2022/039678.
PathFinder Digital, "Free Space Optics vs. Fiber Optics", 2023.
International Search Report and Written Opinion, issued in Application Serial No. PCT/US2023/016152, dated Jul. 12, 2023.
AccuCoat, "Beamsplitter: Divide, combine & conquer"; 2023.
Lin et al., "Photoacoustic imaging", Science Direct; 2021.
Zhou et al., "Photoacoustic Imaging with fiber optic technology: A review", Science Direct; 2020.
International Search Report and Written Opinion issued by the European Patent Office, for Serial No. PCT/US2022/053775, dated Apr. 21, 2023. (Re 45PCT).
International Search Report and Written Opinion issued by the European Patent Office, for Serial No. PCT/US2023/011497, dated Apr. 28, 2023. (Re 54PCT).
International Search Report and Written Opinion issued by the European Patent Office, for Serial No. PCT/US2023/012599, dated May 19, 2023. (Re 57PCT).
International Search Report and Written Opinion dated Apr. 4, 2022 in PCT Application Serial No. PCT/US2021/062170.
International Search Report and Written Opinion dated Apr. 4, 2022 in PCT Application Serial No. PCT/US2021/065073.
Partial Search Report and Provisional Opinion dated May 3, 2022 in PCT Application No. PCT/US2022/015577.
International Search Report and Written Opinion dated May 13, 2022 in PCT Application Serial No. PCT/US2022/017562.
Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.
Jones, H. M., et al. "Pulsed dielectric breakdown of pressurized water and salt solutions", Journal of Applied Physics, Jun. 1998, pp. 795-805, vol. 77, No. 2, American Institute of Physics.
Kozulin, I., et al. "The dynamic of the water explosive vaporization on the flat microheater", Journal of Physics: Conference Series, 2018, pp. 1-4, IOP Publishing, Russia.
Cross, F., "Laser Angioplasty", Vascular Medicine Review, 1992, pp. 21-30, Edward Arnold.
Doukas, A. G., et al. "Laser-generated stress waves and their effects on the cell membrane", IEEE Journal of Selected Topics in Quantum Electronics, 1999, pp. 997-1003, vol. 5, Issue 4, IEEE.
Noack, J., et al. "Laser-Induced Plasma Formation in Water at Nanosecond to Femtosecond Time Scales: Calculation of Thresholds, Absorption Coefficients, and Energy Density", IEEE Journal of Quantum Electronics, 1999, pp. 1156-1167, vol. 35, No. 8, IEEE.
Pratsos, A., "The use of Laser for the treatment of coronary artery disease", Bryn Mawr Hospital, 2010.
Li, Xian-Dong, et al. "Influence of deposited energy on shock wave induced by underwater pulsed current discharge", Physics of Plasmas, 2016, vol. 23, American Institute of Physics.
Logunov, S., et al. "Light diffusing optical fiber illumination", Renewable Energy and the Environment Congress, 2013, Corning, NY, USA.
Maxwell, A. D., et al. "Cavitation clouds created by shock scattering from bubbles during histotripsy", Acoustical Society of America, 2011, pp. 1888-1898, vol. 130, No. 4, Acoustical Society of America.
McAteer, James A., et al. "Ultracal-30 Gypsum Artificial Stones For Research On The Mechinisms Of Stone Breakage In Shock Wave Lithotripsy", 2005, pp. 429-434, Springer-Verlag.
Vogel, A., et al. "Mechanisms of Intraocular Photodisruption With Picosecond and Nanosecond Laser Pulses", Lasers in Surgery and Medicine, 1994, pp. 32-43, vol. 15, Wiley-Liss Inc., Lubeck, Germany.
Vogel, A., et al. "Mechanisms of Pulsed Laser Ablation of Biological Tissues", Chemical Reviews, 2003, pp. 577-644, vol. 103, No. 2, American Chemical Society.
Medlight, "Cylindrical light diffuser Model RD-ML", Medlight S.A., Switzerland.
Medlight, "Cylindircal light diffuser Model RD", Medlight S.A., Switzerland.
Mayo, Michael E., "Interaction of Laser Radiation with Urinary Calculi", Cranfield University Defense and Security, PhD Thesis, 2009, Cranfield University.
Mirshekari, G., et al. "Microscale Shock Tube", Journal of Microelectromechanical Systems, 2012, pp. 739-747, vol. 21, No. 3, IEEE.
"Polymicro Sculpted Silica Fiber Tips", Molex, 2013, Molex.
Zhou, J., et al. "Optical Fiber Tips and Their Applications", Polymicro Technologies A Subsidiary of Molex, Nov. 2007.
Liang, Xiao-Xuan, et al. "Multi-Rate-Equation modeling of the energy spectrum of laser-induced conduction band electrons in water", Optics Express, 2019, vol. 27, No. 4, Optical Society of America.
Nachabe, R., et al. "Diagnosis of breast cancer using diffuse optical spectroscopy from 500 to 1600 nm: comparison of classification methods", Journal of Biomedical Optics, 2011, vol. 16(8), SPIE.
Naugol'nykh, K. A., et al. "Spark Discharges in Water", Academy of Sciences USSR Institute of Acoustics, 1971, Nauka Publishing Co., Moscow, USSR.
Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.
Nyame, Yaw A., et al. "Kidney Stone Models for In Vitro Lithotripsy Research: A Comprehensive Review", Journal of Endourology, Oct. 2015, pp. 1106-1109, vol. 29, No. 10, Mary Ann Liebert Inc., Cleveland, USA.
Ohl, Siew-Wan, et al. "Bubbles with shock waves and ultrasound: a review", Interface Focus, pp. 1-15, vol. 5, The Royal Society Publishing.
Zheng, W., "Optical Lenses Manufactured on Fiber Ends", IEEE, 2015, Splicer Engineering, Duncan SC USA.
Dwyer, P. J., et al. "Optically integrating balloon device for photodynamic therapy", Lasers in Surgery and Medicine, 2000, pp. 58-66, vol. 26, Issue 1, Wiley-Liss Inc., Boston MA USA.
"The New Optiguide DCYL700 Fiber Optic Diffuser Series", Optiguide Fiber Optic Spec Sheet, Pinnacle Biologics, 2014, Pinnacle Biologics, Illinois, USA.
Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.
Oshita, D., et al. "Characteristic of Cavitation Bubbles and Shock Waves Generated by Pulsed Electric Discharges with Different Voltages", IEEE, 2012, pp. 102-105, Kumamoto, Japan.
Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.

(56) References Cited

OTHER PUBLICATIONS

Murray, A., et al. “Peripheral laser angioplasty with pulsed dye laser and ball tipped optical fibres”, The Lancet, 1989, pp. 1471-1474, vol. 2, Issue 8678-8679.
Mohammadzadeh, M., et al. “Photoacoustic Shock Wave Emission and Cavitation from Structured Optical Fiber Tips”, Applied Physics Letters, 2016, vol. 108, American Institute of Physics Publishing LLC.
Doukas, A. G., et al. “Physical characteristics and biological effects of laser-induced stress waves”, Ultrasound in Medicine and Biology, 1996, pp. 151-164, vol. 22, Issue 2, World Federation for Ultrasound in Medicine and Biology, USA.
Doukas, A. G., et al. “Physical factors involved in stress-wave-induced cell injury: the effect of stress gradient”, Ultrasound in Medicine and Biology, 1995, pp. 961-967, vol. 21, Issue 7, Elsevier Science Ltd., USA.
Piedrahita, Francisco S., “Experimental Research Work On A Sub-Millimeter Spark-Gap For Sub Nanosecond Gas Breakdown”, Thesis for Universidad Nacional De Colombia, 2012, Bogota, Colombia.
Vogel, A., et al. “Plasma Formation in Water by Picosecond and Nanosecond Nd: YAG Laser Pulses—Part I: Optical Breakdown at Threshold and Superthreshold Irradiance”, IEEE Journal of Selected Topics in Quantum Electronics, 1996, pp. 847-859, vol. 2, No. 4, IEEE.
Park, Hee K., et al. “Pressure Generation and Measurement in the Rapid Vaporization of Water on a Pulsed-Laser-Heated Surface”, Journal of Applied Physics, 1996, pp. 4072-4081, vol. 80, No. 7, American Institute of Physics.
Cummings, Joseph P., et al. “Q-Switched laser ablation of tissue: plume dynamics and the effect of tissue mechanical properties”, SPIE, Laser-Tissue Interaction III, 1992, pp. 242-253, vol. 1646.
Lee, Seung H., et al. “Radial-firing optical fiber tip containing conical-shaped air-pocket for biomedical applications”, Optics Express, 2015, vol. 23, No. 16, Optical Society of America.
Hui, C., et al. “Research on sound fields generated by laser-induced liquid breakdown”, Optica Applicata, 2010, pp. 898-907, vol. XL, No. 4, Xi’an, China.
Riel, Louis-Philippe, et al. “Characterization of Calcified Plaques Retrieved From Occluded Arteries and Comparison with Potential Artificial Analogues”, Proceedings of the ASME 2014 International Mechanical Engineering Congress and Exposition, 2014, pp. 1-11, ASME, Canada.
Roberts, Randy M., et al. “The Energy Partition of Underwater Sparks”, The Journal of the Acoustical Society of America, 1996, pp. 3465-3475, vol. 99, No. 6, Acoustical Society of America.
Rocha, R., et al. “Fluorescence and Reflectance Spectroscopy for Identification of Atherosclerosis in Human Carotid Arteries Using Principal Components Analysis”, Photomedicine and Lsser Surgery, 2008, pp. 329-335, vol. 26, No. 4, Mary Ann Liebert Inc.
Scepanovic, Obrad R., et al. “Multimodal spectroscopy detects features of vulnerable atherosclerotic plaque”, Journal of Biomedical Optics, 2011, pp. 1-10, vol. 16, No. 1, SPIE.
Serruys, P. W., et al. “Shaking and Breaking Calcified Plaque Lithoplasty, a Breakthrough in Interventional Armamentarium?”, JACC: Cardiovascular Imaging, 2017, pp. 907-911, vol. 10, No. 8, Elsevier.
Vogel, A., et al. “Shock wave emission and cavitation bubble generation by picosecond and nanosecond optical breakdown in water”, The Journal of the Acoustical Society of America, 1996, pp. 148-165, vol. 100, No. 1, Acoustical Society of America.
Vogel, A., et al. “Shock-Wave Energy and Acoustic Energy Dissipation After Laser-induced Breakdown”, SPIE, 1998, pp. 180-189, vol. 3254, SPIE.
International Search Report and Written Opinion, issued by the EP/ISA, in PCT/US2021/048819, dated Jan. 14, 2022.
International Search Report and Written Opinion dated Jun. 28, 2022, in PCT Application Serial No. PCT/US2022/015577.
International Search Report and Written Opinion dated Jun. 27, 2022, in PCT Application Serial No. PCT/US2022/022460.
Medlight, “Cylindrical light diffuser Model RD-ML”, Medlight S.A., Switzerland. 2015. (This reference was cited in a prior Information Disclosure Statement. However, the relevant date was missing. The date has now been added.).
Medlight, “Cylindircal light diffuser Model RD”, Medlight S.A., Switzerland. 2015. (This reference was cited in a prior Information Disclosure Statement. However, the relevant date was missing. The date has now been added.).
Ohl, Siew-Wan, et al. “Bubbles with shock waves and ultrasound: a review”, Interface Focus, pp. 1-15, vol. 5, The Royal Society Publishing. Oct. 2015. (This reference was cited in a prior Information Disclosure Statement. However, the relevant date was missing. The date has now been added.).
Schafter+Kirchhoff, Laser Beam Couplers series 60SMS for coupling into single-mode and polarization-maintaining fiber cables, Schafter+Kirchhoff, pp. 1-5, Germany. Dec. 2, 2021. (This reference was cited in a prior Information Disclosure Statement. However, the relevant date was missing. The date has now been added.).
Meng et al., “Accurate Recovery Of Atrial Endocardial Potential Maps From Non-contact Electrode Data.” Auckland Bioengineering Institute. (ID 1421). May 2019. (This reference was cited in a prior Information Disclosure Statement. However, the relevant date was missing. The date has now been added.).
Jiang et al., “Multielectrode Catheter For Substrate Mapping For Scar-related VT Ablation: A Comparison Between Grid Versus Linear Configurations.” UChicago Medicine, Center for Arrhythmia Care, Chicago IL (ID 1368). Poster for conference in San Francisco, May 8-11, 2019. (This reference was cited in a prior Information Disclosure Statement. However, the relevant date was missing. The date has now been added.).
Sacher et al., “Comparison Of Manual Vs Automatic Annotation To Identify Abnormal Substrate For Scar Related VT Ablation.” LIRYC Institute, Bordeaux University Hospital, France (ID 1336). Poster for conference in San Francisco, May 8-11, 2019. (This reference was cited in a prior Information Disclosure Statement. However, the relevant date was missing. The date has now been added.).
International Search Report and Written Opinion, PCT Application Serial No. PCT/US2022/047751 issued Feb. 10, 2023, by the European Patent Office. (56PCT).
Shen, Yajie et al. “High-peak-power and narrow-linewidth Q-switched Ho: YAG laser in-band pumped at 1931 nm.” Applied Physics Express 13.5 (2020): 052006. (Year 2020).
International Search Report and Written Opinion dated Aug. 25, 2022 in PCT Application Serial No. PCTUS/2022/028035.
International Search Report and Written Opinion dated Sep. 15, 2022 in PCT Application Serial No. PCTUS/2022/032045.
Davletshin, Yevgeniy R., “A Computational Analysis of Nanoparticle-Mediated Optical Breakdown”, A dissertation presented to Ryerson University in Partial Fulfillment of the requirements for the degree of Doctor of Philosophy in the Program of Physics, Toronto, Ontario, CA 2017.
Vogel, A., et al. “Acoustic transient generation by laser-produced cavitation bubbles near solid boundaries”, Journal Acoustical Society of America, 1988, pp. 719-731, vol. 84.
Asshauer, T., et al. “Acoustic transient generation by holmium-laser-induced cavitation bubbles”, Journal of Applied Physics, Nov. 1, 1994, pp. 5007-5013, vol. 76, No. 9, American Institute of Physics.
Zheng, W., “Optic Lenses Manufactured on Fiber Ends”, 2015, Splicer Engineering AFL, Duncan, SC USA.
Ali, Ziad A., et al. “Optical Coherence Tomography Characterization of Coronary Lithoplasty for Treatment of Calcified Lesions”, JACC: Cardiovascular Imaging, 2017, pp. 897-906, vol. 109, No. 8, Elsevier.
Ali, Ziad A., et al. “Intravascular lithotripsy for treatment of stent underexpansion secondary to severe coronary calcification” 2018, European Society of Cardiology.
Ashok, Praveen C., et al. “Raman spectroscopy bio-sensor for tissue discrimination in surgical robotics—full article”, Journal of Biophotonics, 2014, pp. 103-109, vol. 7, No. 1-2.
Ashok, Praveen C., et al. “Raman spectroscopy bio-sensor for tissue discrimination in surgical robotics—proof” Journal of Biophotonics 7, 2014, No. 1-2.

(56) References Cited

OTHER PUBLICATIONS

Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.
Bian, D. C., et al. "Study on Breakdown Delay Characteristics Based on High-voltage Pulse Discharge in Water with Hydrostatic Pressure", Journal of Power Technologies 97(2), 2017, pp. 89-102.
Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.
Brodmann, Marianne et al. "Safety and Performance of Lithoplasty for Treatment of Calcified Peripheral Artery Lesions", JACC, 2017, vol. 70, No. 7.
Brouillette, M., "Shock Waves at Microscales", 2003, pp. 3-12, Springer-Verlag.
Mirshekari, G., et al. "Shock Waves in Microchannels", 2013, pp. 259-283, vol. 724, Cambridge University Press.
"Bubble Dynamics and Shock Waves", Springer, 2013, Springer-Verlag, Berlin Heildelberg.
Hardy, Luke A., et al. "Cavitation Bubble Dynamics During Thulium Fiber Laser Lithotripsy", SPIE, Feb. 29, 2016, vol. 9689, San Francisco, California, USA.
Claverie, A., et al. "Experimental characterization of plasma formation and shockwave propagation induced by high power pulsed underwater electrical discharge", Review of Scientific Instruments, 2014, American Institute of Physics.
Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.
Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.
Cook, Jason R., et al. "Tissue mimicking phantoms for photoacoustic and ultrasonic imaging", Biomedical Optics Express, 2011, vol. 2, No. 11, Optical Society of America.
Deckelbaum, Lawrence I., "Coronary Laser Angioplasty", Lasers in Surgery and Medicine, 1994, pp. 101-110, Wiley-Liss Inc.
Costanzo, F., "Underwater Explosion Phenomena and Shock Physics", Research Gate, 2011.
Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.
De Silva, K., et al. "A Calcific, Undilatable Stenosis Lithoplasty, a New Tool in the Box?", JACC: Cardiovascular Interventions, 2017, vol. 10, No. 3, Elsevier.
Vesselov, L., et al. "Design and performance of thin cylindrical diffusers created in Ge-doped multimode optical fibers", Applied Optics, 2005, pp. 2754-2758, vol. 44, Issue 14, Optical Society of America.
Hutchens, Thomas C., et al. "Detachable fiber optic tips for use in thulium fiber laser lithotripsy", Journal of Biomedical Optics, Mar. 2013, vol. 18(3), SPIE.
Kostanski, Kris L., et al. "Development of Novel Tunable Light Scattering Coating Materials for Fiber Optic Diffusers in Photodynamic Cancer Therapy", Journal of Applied Polymer Science, 2009, pp. 1516-1523, vol. 112, Wiley InterScience.
Kristiansen, M., et al. "High Voltage Water Breakdown Studies", DoD, 1998, Alexandria, VA, USA.
Dwyer, J. R., et al. "A study of X-ray emission from laboratory sparks in air at atmospheric pressure", Journal of Geophysical Research, 2008, vol. 113, American Geophysical Union.
Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.
Shangguan, HanQun et al. "Effects of Material Properties on Laser-induced Bubble Formation in Absorbing Liquids and On Submerged Targets", SPIE, 1997, pp. 783-791, vol. 2869.
Varghese, B., et al. "Effects of polarization and absorption on laser induced optical breakdown threshold for skin rejuvenation", SPIE, Mar. 9, 2016, vol. 9740, SPIE, San Francisco, USA.
Varghese, B., et al. "Effects of polarization and apodization on laser induced optical breakdown threshold", Optics Express, Jul. 29, 2013, vol. 21, No. 15, Optical Society of America.
Bonito, Valentina, "Effects of polarization, plasma and thermal initiation pathway on irradiance threshold of laser Induced optical breakdown", Philips Research, 2013, The Netherlands.
Vogel, A. et al. "Energy balance of optical breakdown in water at nanosecond to femtosecond time scales", Applied Physics B 68, 1999, pp. 271-280, Springer-Verlag.
Kang, Hyun W., et al. "Enhanced photocoagulation with catheter based diffusing optical device", Journal of Biomedical Optics, Nov. 2012, vol. 17(11), SPIE.
Esch, E., et al. "A Simple Method For Fabricating Artificial Kidney Stones Of Different Physical Properties", National Institute of Health Public Access Author Manuscript, Aug. 2010.
Isner, Jeffrey M., et al. "Excimer Laser Atherectomy", Circulation, Jun. 1990, vol. 81, No. 6, American Heart Association, Dallas, TX, USA.
Israel, Douglas H., et al. "Excimer Laser-Facilitated Balloon Angioplasty of a Nondilateable Lesion", JACC, Oct. 1991, vol. 18, No. 4, American College of Cardiology, New York, USA.
Van Leeuwen, Ton G., et al. "Excimer Laser Induced Bubble: Dimensions, Theory, and Implications for Laser Angioplasty", Lasers in Surgery and Medicine 18, 1996, pp. 381-390, Wiley-Liss Inc., Utrecht, The Netherlands.
Nguyen, H., et al. "Fabrication of multipoint side-firing optical fiber by laser micro-ablation", Optics Letters, May 1, 2017, vol. 42, No. 9, Optical Society of America.
Zheng, W., "Optic Lenses Manufactured on Fiber Ends", 2015, IEEE, Duncan, SC, USA.
Whitesides, George M., et al. "Fluidic Optics", 2006, vol. 6329, SPIE, Cambridge, MA, USA.
Forero, M., et al. "Coronary lithoplasty: a novel treatment for stent underexpansion", Cardiovascular Flashlight, 2018, European Society of Cardiology.
Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.
Roberts, Randy M., et al. "The Energy Partition of Underwater Sparks", The Journal of the Acoustical Society of America, Jun. 1996, pp. 3465-3474, Acoustical Society of America, Austin, TX, USA.
Blackmon, Richard L., et al. "Holmium: YAG Versus Thulium Fiber Laser Lithotripsy", Lasers in Surgery and Medicine, 2010, pp. 232-236, Wiley-Liss Inc.
Varghese, B., "Influence of absorption induced thermal initiation pathway on irradiance threshold for laser induced breakdown", Biomedical Optics Express, 2015, vol. 6, No. 4, Optical Society of America.
Noack, J., "Influence of pulse duration on mechanical effects after laser-induced breakdown in water", Journal of Applied Physics, 1998, pp. 7488-EOA, vol. 83, American Institute of Physics.
Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.
"Custom Medical Skived Tubing", Duke Extrusion, 2025. https://www.dukeextrusion.com/tubing-options/skived-tubing.
Definition of ablation—NCI Dictionary of Cancer Terms—NCI, National Cancer Institute, p. 1 (Year:2025).
Daemen, J., Tovar Forero, M.N, "The Coronary Intravascular Lithotripsy System", ICR Journal, 2019; 14(3); 174-181.

(56) References Cited

OTHER PUBLICATIONS

Butt, N., Khalid, N., Shlofmitz, E., "Intravascular Lithotripsy"; NCBI Bookshelf. A service of the National Library of Medicine, National Institutes of Health; StatPearls Publishing, 2023.

* cited by examiner

OPTICAL ASSEMBLIES TO IMPROVE ENERGY COUPLING TO PRESSURE WAVE GENERATOR OF AN INTRAVASCULAR LITHOTRIPSY DEVICE

RELATED APPLICATION

This application claims priority from U.S. Provisional Application Ser. No. 63/148,133, filed on Feb. 10, 2021. To the extent permitted, the contents of U.S. Provisional Application Ser. No. 63/148,133 are incorporated in their entirety herein by reference.

BACKGROUND

Vascular lesions within and adjacent to vessels in the body can be associated with an increased risk for major adverse events, such as myocardial infarction, embolism, deep vein thrombosis, stroke, and the like. Severe vascular lesions can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

Using optical fiber delivery of laser pulses to generate high-pressure impulses on the lesions is one way to attempt to treat the lesions. The creation of plasma via optical breakdown of an aqueous solution typically requires a significant amount of energy in a short amount of time upon which it is converted into a therapeutic bubble and/or a therapeutic pressure wave.

SUMMARY

The present invention is directed toward a catheter system for treating a treatment site within or adjacent to a vessel wall or a heart valve. The catheter system includes an inflatable balloon, an optical fiber, and an energy source. In certain embodiments, the optical fiber has (i) a fiber proximal end and (ii) a fiber distal end positioned within the inflatable balloon. The optical fiber can be configured to receive an energy pulse so that the optical fiber emits light energy in a direction away from the optical fiber to generate a plasma pulse within the inflatable balloon, the optical fiber being tapered from the fiber proximal end to the fiber distal end. The energy source can be in optical communication with the fiber proximal end of the optical fiber.

In various embodiments, the optical fiber can be tapered using a fusion splicer.

In certain embodiments, the optical fiber can be spliced using a core matched fiber.

In some embodiments, the optical fiber can be split into a first fiber member and a second fiber member.

In various embodiments, the optical fiber can be split so that only the second fiber member can be positioned within the inflatable balloon.

In certain embodiments, the second fiber member can include a plurality of second fiber legs.

In some embodiments, the second fiber member can include two second fiber legs.

In various embodiments, the second fiber member can include three second fiber legs.

In certain embodiments, the first fiber member can be fused to the second fiber member in a fused region.

In some embodiments, the first fiber member and the second fiber member are formed as a unitary structure.

In various embodiments, the first fiber member and the second fiber member are integrally formed with one another.

In certain embodiments, the first fiber member and the second fiber member are continuously formed as a single structure.

In some embodiments, the first fiber member can have a first fiber member distal region that is outside the inflatable balloon. In some embodiments, the tapered portion can be proximal of the inflatable balloon. For example, the tapered portion can be proximal of the inflatable balloon when the tapered portion is included on the first fiber member.

In various embodiments, the second fiber member can have a second fiber member proximal region that is outside the inflatable balloon.

In certain embodiments, the first fiber member distal region can be fused to the second fiber member proximal region in the fused region.

In some embodiments, the energy source can include a laser.

In various embodiments, the catheter system can include a ferrule that encircles the fused region.

In certain embodiments, the catheter system can include a ferrule that encircles a first fiber proximal end of the first optical fiber and the first fiber distal end of the second fiber.

In some embodiments, the catheter system can include a plurality of ferrules that encircle portions of the first fiber member and the second fiber member.

In various embodiments, the ferrule can have an outer diameter of 1.25 mm LC ferrules.

In certain embodiments, the ferrule can have an outer diameter of 2.5 mm SC ferrules.

In some embodiments, the ferrule can be formed by one of a plastic and a metal.

In various embodiments, the ferrule can be configured for only one optical fiber.

In certain embodiments, the ferrule can be configured for a plurality of fiber members.

In some embodiments, the ferrule can be one of a multi-fiber MT ferrule and an MTP ferrule.

In various embodiments, the optical fiber can be cleaved at a first tapered portion of the first fiber member.

In certain embodiments, the optical fiber can be cleaved by one of a laser cleaver and a mechanical cleaver.

In some embodiments, the first fiber member can have a first cleaved portion that can be cleaved a second time to form a curved ball surface.

In various embodiments, the optical fiber can be tapered with rotation.

In certain embodiments, the optical fiber can be tapered without rotation.

In some embodiments, the ferrule can include at least one of a tapered fiber, a spliced joint, and a bare fiber.

In various embodiments, at least one of the tapered fiber, the spliced joint, and the bare fiber are retained inside the ferrule with an epoxy.

In certain embodiments, the epoxy can be ND353 encircled for fiber connector polishing.

In some embodiments, the epoxy can be LOCTITE® 4310 UV adhesive.

In various embodiments, the optical fiber can be tapered from a diameter of 200 μm to a diameter of 105 μm.

In certain embodiments, the optical fiber can be configured to split a light energy traveling through the first fiber member into the second fiber member.

In some embodiments, the first fiber member can include an endcap.

In various embodiments, the ferrule substantially surrounds the first fiber member.

In certain embodiments, the optical fiber can be tapered so that it can have a greater diameter on the fiber proximal end and a lesser diameter on the fiber distal end.

The present invention is also directed toward a method for manufacturing the catheter system.

The present invention is further directed toward a method for treating a treatment site within or adjacent to a vessel wall or heart valve. The method can include the steps of positioning an optical fiber having (i) a fiber proximal end and (ii) a fiber distal end positioned within the inflatable balloon, the optical fiber being configured to receive an energy pulse so that the optical fiber emits light energy in a direction away from the optical fiber to generate a plasma pulse within the inflatable balloon, and coupling an energy source with the fiber proximal end of the optical fiber so that the energy source is in optical communication with the optical fiber.

In some embodiments, the method can include the step of tapering the optical fiber using a fusion splicer.

In various embodiments, the method can include the step of splicing the optical fiber using a core matched fiber.

In certain embodiments, the method can include the step of encircling the fused region using a ferrule.

In some embodiments, the method can include the step of encircling a first fiber distal end of the first fiber member and the second fiber proximal end of the second fiber member using a ferrule.

In various embodiments, the method can include the step of encircling portions of the first fiber member and the second fiber member using a plurality of ferrules.

The present invention is also directed toward a catheter system that includes an inflatable balloon, an optical fiber, an energy source, and a fused region. The optical fiber can have (i) a fiber proximal end and (ii) a fiber distal end positioned within the inflatable balloon. The optical fiber can be configured to receive an energy pulse so that the optical fiber emits light energy in a direction away from the optical fiber to generate a plasma pulse within the inflatable balloon. The optical fiber can include a first fiber member and a second fiber member. The energy source can be in optical communication with the fiber proximal end of the optical fiber. The fused region can be located where the first fiber member is fused to the second fiber member.

The present invention is further directed toward a catheter system that includes an inflatable balloon, an optical fiber, an energy source, and a fused region. The optical fiber can have (i) a fiber proximal end and (ii) a fiber distal end positioned within the inflatable balloon. The optical fiber can be configured to receive an energy pulse so that the optical fiber emits light energy in a direction away from the optical fiber to generate a plasma pulse within the inflatable balloon. The optical fiber can have a first fiber member and a second fiber member including a plurality of second fiber member legs. The energy source can be in optical communication with the fiber proximal end of the optical fiber. The fused region can be located where the first fiber member is fused to the second fiber member. The fused region can be configured to split the light energy traveling through the first fiber member into the second fiber member so that the light energy is split between the plurality of the second fiber member legs.

The present invention is also directed toward a catheter system that includes an inflatable balloon, an optical fiber, an energy source, a fused region, and a capillary. The optical fiber can have (i) a fiber proximal end and (ii) a fiber distal end positioned within the inflatable balloon. The optical fiber can be configured to receive an energy pulse so that the optical fiber emits light energy in a direction away from the optical fiber to generate a plasma pulse within the inflatable balloon. The optical fiber can have a first fiber member and a second fiber member including a plurality of second fiber member legs. The energy source can be in optical communication with the fiber proximal end of the optical fiber. The fused region can be located where the first fiber member is fused to the second fiber member. The fused region can be configured to split the light energy traveling through the first fiber member into the second fiber member so that the light energy is split between the plurality of the second fiber member legs. The capillary can substantially surround the fused region.

The present invention is further directed toward a catheter system that includes an inflatable balloon, an optical fiber, a fused region, and a ferrule. The optical fiber can have (i) a fiber proximal end and (ii) a fiber distal end positioned within the inflatable balloon. The optical fiber can be configured to receive an energy pulse so that the optical fiber emits light energy in a direction away from the optical fiber to generate a plasma pulse within the inflatable balloon. The optical fiber can include an endcap and a first fiber distal end positioned within the inflatable balloon. The optical fiber can have a first fiber member and a second fiber member. The fused region can be located where the first fiber member is fused to the second fiber member. The ferrule can substantially surround the fused region.

The present invention is also directed toward a catheter system that includes an inflatable balloon, an optical fiber, an energy source, a fused region, and a ferrule. The optical fiber can have (i) a fiber proximal end, and (ii) a fiber distal end positioned within the inflatable balloon. The optical fiber can be configured to receive an energy pulse so that the optical fiber emits light energy in a direction away from the optical fiber to generate a plasma pulse within the inflatable balloon. The optical fiber can include a first fiber member and a second fiber member. The energy source can be in optical communication with the fiber proximal end of the optical fiber. The fused region can be located where the first fiber member is fused to the second fiber member. The ferrule can substantially surround the first fiber member and the fused region.

The present invention is further directed toward a catheter system that includes an inflatable balloon and an optical fiber. The optical fiber can have (i) a fiber proximal end, and (ii) a fiber distal end positioned within the inflatable balloon. The optical fiber can be configured to receive an energy pulse so that the optical fiber emits light energy in a direction toward the fiber distal end to generate a plasma pulse within the inflatable balloon. The optical fiber can be tapered so that it can have a greater diameter on the fiber proximal end and a lesser diameter on the fiber distal end.

The present invention is also directed toward a catheter system that includes an inflatable balloon and an optical fiber. The optical fiber can have (i) a fiber proximal end, and (ii) a fiber distal end positioned within the inflatable balloon. The optical fiber can be configured to receive an energy pulse so that the optical fiber emits light energy in a direction away from the optical fiber to generate a plasma pulse within the inflatable balloon. The optical fiber can be tapered from the fiber proximal end to the fiber distal end. The energy source can be in optical communication with the fiber proximal end of the optical fiber.

The present invention is further directed toward a catheter system that includes an inflatable balloon and an optical fiber. The optical fiber can have (i) a fiber proximal end, and (ii) a fiber distal end positioned within the inflatable balloon. The optical fiber can be configured to receive an energy pulse so that the optical fiber emits light energy in a direction away from the optical fiber to generate a plasma pulse within the inflatable balloon. The optical fiber can be split into a plurality of fiber members positioned within the inflatable balloon. The energy source can be in optical communication with the fiber proximal end of the optical fiber.

In various embodiments, the optical fiber can be tapered from a diameter of 220 μm to a diameter of 100 μm.

In some embodiments, the optical fiber can be tapered from (i) an initial diameter to (ii) a final diameter having a diameter of 90% to 10% of the initial diameter.

In certain embodiments, the catheter system can include a third fiber member and a second fused region, the third fiber member being fused to the second fiber member in the second fused region, the second fiber member further including a second tapered portion.

The present invention is also directed toward a catheter system for treating a treatment site within or adjacent to a vessel wall or heart valve. The catheter system can include an inflatable balloon, an optical fiber, an energy source, a first tapered portion, a second tapered portion, a first fused region, a second fused region, and a ferrule. The optical fiber can have (i) a fiber proximal end, and (ii) a fiber distal end positioned within the inflatable balloon, the optical fiber being configured to receive an energy pulse so that the optical fiber emits light energy in a direction away from the optical fiber to generate a plasma pulse within the inflatable balloon, the optical fiber having a first fiber member, a second fiber member, and a third fiber member. The energy source can be optical communication with the fiber proximal end of the optical fiber. The first tapered portion can be located on the first fiber member. The second tapered portion can be located on the second fiber member. The first fused region where the first fiber member is fused to the second fiber member. The second fused region can be where the second fiber member is fused to the third fiber member. The ferrule can substantially surround the first fiber member and the first fused region.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 3AA is a cross-sectional view of the optical fiber taken on line 3AA-3AA in FIG. 3A;

FIG. 3BB is a cross-sectional view of the optical fiber taken on line 3BB-3BB in FIG. 3B;

Figure 1:
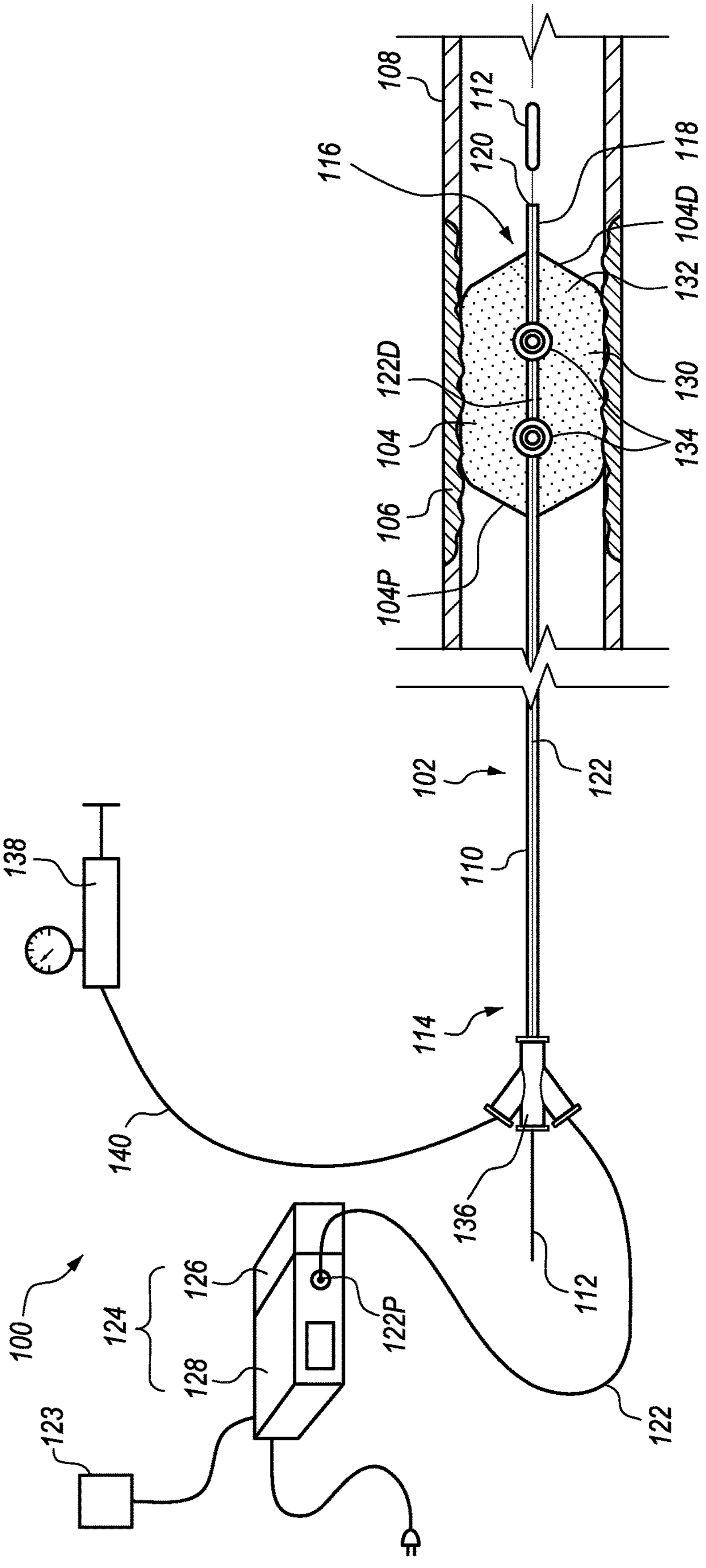
FIG. 1 is a schematic cross-sectional view of one embodiment of a catheter system having features of the present invention.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DESCRIPTION

Treatment of vascular lesions can reduce major adverse events or death in affected subjects. A major adverse event is one that can occur anywhere within the body due to the presence of a vascular lesion. Major adverse events can include, but are not limited to major adverse cardiac events, major adverse events in the peripheral or central vasculature, major adverse events in the brain, major adverse events in the musculature, or major adverse events in any of the internal organs.

As used herein, the treatment site can include a vascular lesion such as a calcified vascular lesion or a fibrous vascular lesion (hereinafter sometimes referred to simply as a "lesion" or "treatment site"), typically found in a blood vessel and/or a heart valve. Plasma formation can initiate a pressure wave and can initiate the rapid formation of one or more bubbles that can rapidly expand to a maximum size and then dissipate through a cavitation event that can also launch a pressure wave upon collapse. The rapid expansion of the plasma-induced bubbles can generate one or more pressure waves within a balloon fluid and thereby impart pressure waves upon the treatment site. The pressure waves can transfer mechanical energy through an incompressible balloon fluid to a treatment site to impart a fracture force on the lesion. Without wishing to be bound by any particular theory, it is believed that the rapid change in balloon fluid momentum upon a balloon wall of the inflatable balloon that is in contact with or positioned near the lesion is transferred to the lesion to induce fractures in the lesion.

Those of ordinary skill in the art will realize that the following detailed description of the present invention is illustrative only and is not intended to be in any way limiting. Other embodiments of the present invention will readily suggest themselves to such skilled persons having the benefit of this disclosure. Additionally, other methods of delivering energy to the lesion can be utilized, including, but not limited to, the electric current induced plasma generation. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is appreciated that such a development effort might be complex and time-consuming, but would nevertheless be a routine undertaking of engineering for those of ordinary skill in the art having the benefit of this disclosure.

As used herein, the terms "treatment site", "intravascular lesion" and "vascular lesion" are used interchangeably unless otherwise noted and can include lesions located at or near blood vessels or heart valves.

It is appreciated that the catheter systems herein can include many different forms and/or configurations other than those specifically shown and/or described herein. Referring now to FIG. 1, a schematic cross-sectional view is shown of a catheter system in accordance with various embodiments herein. A catheter system 100 is suitable for imparting pressure to induce fractures in a vascular lesion within or adjacent to a vessel wall of a blood vessel and/or a heart valve. In the embodiment illustrated in FIG. 1, the catheter system 100 can include one or more of a catheter 102, one or more optical fibers 122, a controller 123, an energy source 124, a manifold 136, a fluid pump 138, and a multiplexer (not shown).

The catheter 102 includes an inflatable balloon 104 (sometimes referred to herein as "balloon"). The catheter 102 is configured to move to a treatment site 106 within or adjacent to a blood vessel 108. The treatment site 106 can include a vascular lesion such as a calcified vascular lesion, for example. Additionally, or in the alternative, the treatment site 106 can include a vascular lesion such as a fibrous vascular lesion.

The catheter 102 can include the balloon 104, a catheter shaft 110, and a guidewire 112. The balloon can be coupled to the catheter shaft 110. The balloon can include a balloon proximal end 104P and a balloon distal end 104D. The catheter shaft 110 can extend between a shaft proximal end 114 and a shaft distal end 116. The catheter shaft 110 can include a guidewire lumen 118 which is configured to move over the guidewire 112. The catheter shaft 110 can also include an inflation lumen (not shown). In some embodiments, the catheter 102 can have a distal end opening 120 and can accommodate and be moved over and/or along the guidewire 112 so that the balloon 104 is positioned at or near the treatment site 106.

The balloon 104 can include a balloon wall 130. The balloon 104 can expand from a collapsed configuration suitable for advancing at least a portion of the catheter shaft 102 through a patient's vasculature to an expanded configuration suitable for anchoring the catheter 102 into position relative to the treatment site 106.

The catheter shaft 110 of the catheter 102 can encircle one or more optical fibers 122 (only one optical fiber 122 is illustrated in FIG. 1 for clarity) in optical communication with the energy source 124. The optical fiber 122 can be at least partially disposed along and/or within the catheter shaft 110 and at least partially within the balloon 104. In some embodiments, the catheter shaft 110 can encircle multiple optical fibers 122 such as a second optical fiber, a third optical fiber, etc.

The optical fiber 122 can vary depending on the design requirements of the catheter system 100, and/or the energy source 124. It is understood that the optical fiber 122 can include additional systems, subsystems, components, and elements than those specifically shown and/or described herein. Additionally, or alternatively, the optical fiber 122 can omit one or more of the systems, subsystems, and elements that are specifically shown and/or described herein.

The optical fiber 122 has a fiber proximal end 122P that is positioned at or adjacent to the energy source 124, and a fiber distal end 122D that can be positioned within the inflatable balloon 104. The optical fiber 122 extends between the laser 124 and the balloon 104. The optical fiber 122 is in optical communication with the energy source 124. It is appreciated that the optical fiber 122 can be substituted with any suitable light carrier (the optical fiber 122 is a light carrier) configured to carry one or more sub-millisecond energy pulses and/or any suitable energy source.

The controller 123 can control the energy source 124 so that the energy source 124 can generate one or more energy pulses as provided in greater detail herein. The controller 123 may also perform any other relevant functions to control the operation of the catheter 102.

The energy source 124 of the catheter system 100 can be configured to provide one or more sub-millisecond energy pulses that are sent to and received by the optical fiber 122. The optical fiber 122 acts as a conduit for light energy that is generated by the energy pulse(s). In certain embodiments, the energy source 124 (also sometimes referred to herein as a "laser") can include a laser. In some such embodiments, the laser 124 can include one or more seed sources 126 and one or more amplifiers 128. Each amplifier 128 can be in optical communication with at least one of the seed sources 126. The seed source(s) 126 can each emit a relatively low-power seed pulse that is received and amplified by the amplifier 128. The amplifier 128 can increase the power of the seed pulse to generate the energy pulse. In one embodiment, the laser 124 can include one seed source 126 and one amplifier 128.

Alternatively, the laser 124 can include a plurality of seed sources 126 and one amplifier 128. Still alternatively, the laser 124 can include a plurality of seed sources 126 and a plurality of amplifiers 128. It is appreciated that the laser 124 can be substituted with any suitable energy source (the laser 124 is an energy source) configured to provide one or more sub-millisecond energy pulses that are sent to and received by the optical fiber 122.

The light energy that is generated by the energy pulse(s) is delivered by the optical fiber 122 to a location within the balloon 104. The light energy induces plasma formation in the form of a plasma pulse 134 that occurs in the balloon fluid 132 within the balloon 104. The plasma pulse 134 causes rapid bubble formation and imparts pressure waves upon the treatment site 106. Exemplary plasma pulses 134 are shown in FIG. 1. The balloon fluid 132 can be a liquid or a gas. As provided in greater detail herein, the plasma-induced bubbles 134 are intentionally formed at some distance away from the optical fiber 122 so that the likelihood of damage to the optical fiber is decreased.

In various embodiments, the sub-millisecond pulses of light can be delivered to near the treatment site 106 at a frequency of from at least approximately 1 hertz (Hz) up to approximately 5000 Hz. In some embodiments, the sub-millisecond pulses of light can be delivered to near the treatment site 106 at a frequency from at least 30 Hz to 1000 Hz. In other embodiments, the sub-millisecond pulses of light can be delivered to near the treatment site 106 at a frequency from at least 10 Hz to 100 Hz. In yet other embodiments, the sub-millisecond pulses of light can be delivered to near the treatment site 106 at a frequency from at least 1 Hz to 30 Hz.

It is appreciated that the catheter system 100 herein can include any number of optical fibers 122 in optical communication with the laser 124 at the proximal portion 114 and with the balloon fluid 132 within the balloon 104 at the distal portion 116. For example, in some embodiments, the catheter system 100 herein can include 1-30 optical fibers 122. In some embodiments, the catheter system 100 herein can include greater than 30 optical fibers.

The manifold 136 can be positioned at or near the shaft proximal end 114. The manifold 136 can include one or more proximal end openings that can receive the one or more optical fibers, such as optical fiber 122, the guidewire 112, and/or an inflation conduit 140. The catheter system 100 can also include the fluid pump 138 that is configured to inflate the balloon 104 with the balloon fluid 132 and/or deflate the balloon 104 as needed.

The multiplexer (not shown) communicates with a single energy source into one or more of the optical channels in a tightly controlled manner. This approach can allow a single energy source to be channeled sequentially through a plurality of channels with a variable number.

As with all embodiments illustrated and described herein, various structures may be omitted from the figures for clarity and ease of understanding. Further, the figures may include certain structures that can be omitted without deviating from the intent and scope of the invention.

Figure 2:
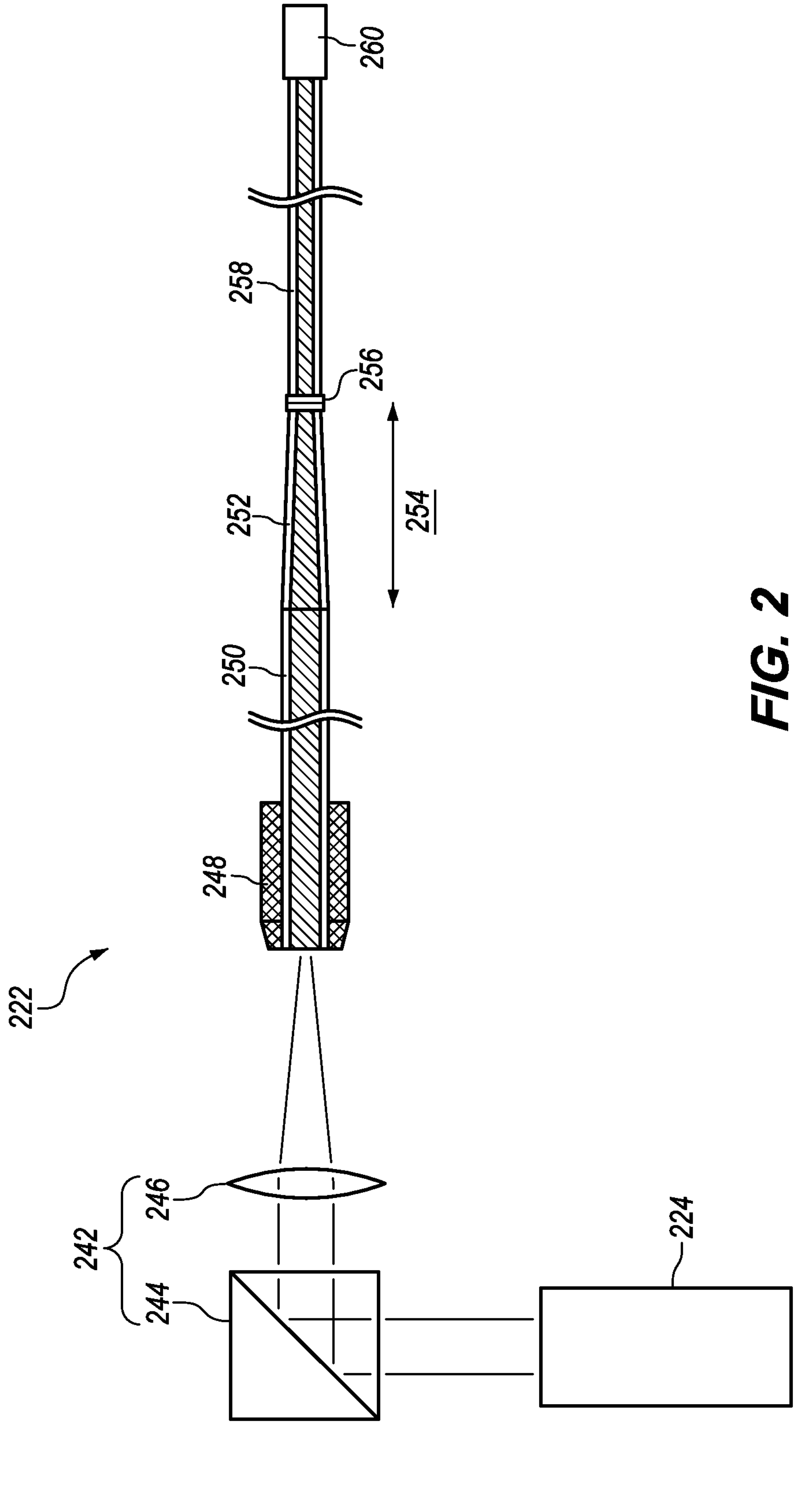
FIG. 2 is a schematic cross-sectional view of one embodiment of a portion of the catheter system including an optical fiber, coupling optics, and an energy source.

FIG. 2 is a schematic cross-sectional view of one embodiment of the optical fiber 222, a coupling optics 242, and an energy source (in the embodiment shown in FIG. 2, the energy source is a laser 224) for use within the catheter system 100. The laser 224 can generate an energy pulse that is directed towards the coupling optics 246. The laser 224 can be a pulsed IR laser or any suitable laser. In various embodiments, the catheter system 100 can include one or more emitter(s) 260 distributed along an active length(s) of the calcified vascular lesion(s) located at the treatment site 106.

The energy source described herein can be any suitable energy source for use within the catheter system 100. In some embodiments, the optical fiber 222 can be substituted with any suitable light carrier configured to receive an energy pulse. The optical fiber 222 can receive the energy pulse and can direct the energy pulse toward the emitter 260.

The coupling optics 242 couple and redirect the energy pulse toward the optical fiber 222. The coupling optics 242 can vary depending on the design requirements of the catheter system 100, the optical fiber 222, and/or the laser 224. It is understood that the coupling optics 242 can include additional systems, subsystems, components, and elements than those specifically shown and/or described herein. Additionally, or alternatively, the coupling optics 242 can omit one or more of the systems, subsystems, and elements that are specifically shown and/or described herein. The coupling optics 242 can include a reflector 244 and a lens 246. The reflector 244 can reflect the energy pulse towards the lens 246. The lens 246 can focus the energy pulse so that the optical fiber 222 is capable of receiving the energy pulse of proper diameter and/or size.

In the embodiment illustrated in FIG. 2, the optical fiber 222 can include a ferrule 248, a first fiber member 250, a tapered portion 252 having a tapered portion length 254, a fused region 256, a second fiber member 258, and an emitter 260.

The ferrule 248 can organize and align the light carrier (e.g., the optical fiber 222) to the coupling optics 242 in the multiplexer (not shown). The ferrule 248 can vary depending on the design requirements of the catheter system 100, the optical fiber 222, and/or the laser 224. It is understood that the ferrule 248 can include additional systems, subsystems, components, and elements than those specifically shown and/or described herein. Additionally, or alternatively, the ferrule 248 can omit one or more of the systems, subsystems, and elements that are specifically shown and/or described herein.

The ferrule 248 can be a rigid member configured to confine and support the optical fiber. The ferrule 248 can also serve as a connector and/or a mechanical splice in the catheter system 199. The ferrule 248 can substantially surround any portion of the optical fiber 222.

In certain embodiments, the system and method described herein can include a segmented light carrier (e.g., the optical fiber 222) that is larger at its fiber proximal end and reduces to a smaller diameter towards the fiber distal end. Alternatively, the light carrier can be larger at the fiber distal end and reduce to a smaller diameter at the fiber proximal end.

The distal section (e.g., the second fiber member 258) can consist of a single light carrier or a plurality of light carriers leading to the emitter(s) 260. The proximal section (e.g., the first fiber member 250) can also consist of a single light carrier or a plurality of light carriers leading to the coupling optics 242. The tapered light carrier can improve pressure wave generation and the catheter system 100 performance.

The first fiber member 250 can be configured to be fixed to the ferrule 248. The first fiber member 250 can be a segment of the optical fiber 222 that is proximal to the laser 224 and the coupling optics 242. The first fiber member 250 can vary depending on the design requirements of the catheter system 100, the optical fiber 222, and/or the laser 224. It is understood that the first fiber member 250 can include additional systems, subsystems, components, and elements than those specifically shown and/or described herein. Additionally, or alternatively, the first fiber member 250 can omit one or more of the systems, subsystems, and elements that are specifically shown and/or described herein.

In certain embodiments, the first fiber member 250 can include the first tapered portion 252. In other embodiments, the first fiber member 250 can be separately attached or coupled to the tapered portion 252. The first fiber member 250 can be tapered and/or otherwise varied to have a modified shape. The first fiber member 250 can be a separate fiber or fiber member that is attached to the tapered portion 252 and/or the second fiber member 258.

The tapered portion 252 can allow for the optical fiber 222 to have a reduced diameter at the distal portion of the optical fiber 222 (e.g., the second fiber member 258). The tapered portion 252 can vary depending on the design requirements of the catheter system 100, the optical fiber 222, and/or the laser 224. The shape, taper, and/or dimensions of the tapered portion 252 can also vary. The tapered portion 252 can have a tapered portion length 254. The tapered portion length 254 can have varying lengths depending on the design requirements of the catheter system 100 and/or the optical fiber.

The location of the tapered portion 252 on the optical fiber 222 can vary. In some embodiments, the tapered portion 252 is located in close proximity to the coupling optics 242. In other embodiments, the tapered portion 252 is located closer to the balloon 104. It is appreciated that the tapered portion 252 can be located at any location along the optical fiber 222. In some embodiments, the optical fiber 222 can include a plurality tapered portions 252, located along varying locations of the optical fiber 222. It is appreciated that the optical fiber 222 can include any number of tapered portions 252 to meet the design requirements of the catheter system 100 and/or optical fiber 222.

The fused region 256 can be formed by fusing the first fiber member 250 with the second fiber member 258. The fused region 256 can join fibers and/or fiber members of different diameters together. In some embodiments, the fused region 256 can be fused around a split and/or spliced portion (shown in FIGS. 3AA and 3BB) of the optical fiber 222, so that the two severed portions of the optical fiber 222 can be joined.

The fused region 256 can vary depending on the design requirements of the catheter system 100, the optical fiber 222, and/or the laser 224. The shape and/or dimensions of fused region 256 can also vary. The location of the fused region 256 on the optical fiber 222 can vary. In some embodiments, the fused region 256 is located in close proximity to the coupling optics 242. In other embodiments, the fused region 256 is located closer to the balloon 104. It is appreciated that the fused region 256 can be located in any location along the optical fiber 222.

The second fiber member 258 can be substantially similar to the first fiber member 250. However, in certain embodiments, the second fiber member 258 can have a smaller diameter than the first fiber member 250. The second fiber member 258 can be a segment of the optical fiber 222 that is distal to the laser 224 and the coupling optics 242. The second fiber member 258 can be in optical communication with the emitter 260.

The second fiber member 258 can vary depending on the design requirements of the catheter system 100, the optical fiber 222, the first fiber member 250, the tapered portion 252, and/or the emitter 260. It is understood that the second fiber member 258 can include additional systems, subsystems, components, and elements than those specifically shown and/or described herein. Additionally, or alternatively, the second fiber member 258 can omit one or more of the systems, subsystems, and elements that are specifically shown and/or described herein.

While the first fiber member 250 and second fiber member 258 are described herein, it is appreciated that the optical fiber 222 can include any number of fiber members. In some embodiments, the optical fiber 222 includes up to fifty fiber members. In other embodiments, the first fiber member 250 having a first tapered portion (not shown) can be fused to a second fiber member 258 having a second tapered portion (not shown) that can be fused to the third fiber member (not shown. The optical fiber 222 can include any number of fiber members that can each have any number of tapered portions and can each include any number of fused sections and/or other attachment points as known in the art.

The emitter 260 can be driven by the energy source. The emitter 260 can be a plasma generator. The optical fiber 222 can include one or more emitters 260. The emitter 260 can be located at any position along the portion of the optical fiber 222 located inside the balloon 104. The emitter 260 can produce one or more plasma pulses 134.

The emitter 260 can vary depending on the design requirements of the catheter system 100, the optical fiber 222, and/or the laser 224. It is understood that the emitter 260 can include additional systems, subsystems, components, and elements than those specifically shown and/or described herein. Additionally, or alternatively, the emitter 260 can omit one or more of the systems, subsystems, and elements that are specifically shown and/or described herein.

One method for tapering the light carrier (e.g., tapering the optical fiber 222) includes tapering the larger proximal section down by heating, drawing, and then cleaving it at the smaller end. The light carrier assembly can be formed by fusing the smaller diameter end to a smaller diameter carrier for the distal section. The light carrier can be fused using a fused joint.

Another embodiment of the tapering method can include heating and drawing the proximal section continuously to make a longer light carrier with a smaller diameter for the distal section. The tapering method can include creating a short, tapered portion 252 and fusing the large end and small end to matching diameter light carriers. This embodiment can require two fused joints.

In certain embodiments, the light carrier (e.g., the optical fiber 222) leading to the laser-driven pressure wave generating device (e.g., the emitter 260) can include three subsections. The proximal section can use a light carrier with a larger core diameter than the distal section. The proximal section of the light carrier begins at diameter $D_p$ and can be tapered or joined to a tapered section that reduces the diameter to match the distal section with diameter $D_d$. The light energy can be coupled into the end face of the proximal section.

The large diameter of the proximal face can reduce the precision required in forming the coupled light energy beam and aligning the coupling optics 242 to the light guide (e.g., the optical fiber 222). This design can reduce the multiplexer accuracy requirements and the optomechanical tolerances for connectorizing the light carrier. The tapered portion 252 can preserve the energy pulse and transmits the energy pulse to the smaller diameter carrier with minimal losses.

In certain embodiments, etendue is conserved in the light guide. Etendue conservation mandates that the product of numerical aperture (NA) and diameter remain constant. As a result, the NA of the distal section of the taper must increase so that $NA_d=(D_p/D_d)\ NA_p$. For example, an optical fiber 222 with an intrinsic NA=0.22 that is tapered from 200 microns to 100 microns increases the NA to NA=0.44. If the smaller diameter end of the taper were fused to a light guide with similar NA=0.22, the mismatch would cause significant coupling losses into the cladding of the smaller fiber.

In various embodiments, the optical fiber 222 can be tapered from 220 microns to 100 microns. The optical fiber 222 described herein can be tapered from an initial diameter of 100 μm, 110 μm, 120 μm, 130 μm, 140 μm, 150 μm, 160 μm, 170 μm, 180 μm, 190 μm, 200 μm, 220 μm, 240 μm, 260 μm, 280 μm, 300 μm, 320 μm, 340 μm, 360 μm, 380 μm, 400 μm, 420 μm, 440 μm, 460 μm, 480 μm, 500 μm, 520 μm, 540 μm, 560 μm, 580 μm, 600 μm, 620 μm, 740 μm, 760 μm, 780 μm, 800 μm, 850 μm, 900 μm, 1 mm or greater than 1 mm to a final diameter of less than 1 μm, 1 μm, 5 μm, 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 220 μm, 240 μm, 260 μm, 280 μm, 300 μm, 320 μm, 340 μm, 360 μm, 380 μm, 400 μm, 420 μm, 440 μm, 460 μm, 480 μm, 500 μm, 520 μm, 540 μm, 560 μm, 580 μm, 600 μm, 620 μm, 740 μm, 760 μm, 780 μm, 800 μm, 850 μm, 900 μm. It is appreciated that the optical fibers and/or light carriers illustrated and/or described herein can be tapered to have final diameters and initial diameters that can fall within a range, wherein any of the foregoing numbers can serve as the lower or upper bound of the range, provided that the lower bound of the range is a value less than the upper bound of the range. The optical fibers and/or light carriers described herein can have final diameters and initial diameters that fall outside of the range described herein.

One method to avoid the coupling losses is to use a light carrier with lower NA on the fiber proximal end having the larger diameter and a light carrier with NA greater by the ratio of diameters for the smaller distal section. The tapering process from $D_p$ down to $D_d$ matches the numerical apertures of the two sections. In some embodiments, the tapered portion 252 can be formed to produce an adiabatic change in light bending and resulting NA to minimize losses through the transition.

Stimulated Brillouin Scattering (SBS) is a non-linear process in the light carrier that can limit total energy transmission. In SBS, an intense beam of light energy can interact with an acoustic wave in the medium, leading to a weak reflected beam. The reflected beam is generally referred to as a Stokes wave, and the original beam can then interfere to amplify the acoustic wave through electrostriction. The power in the reflected beam can increase nonlinearly with input beam power. As a result, energy throughput can be continually reduced with input power, effectively clamping the peak transmitted power which significantly limits the conversion efficiency and yield of the emitter.

SBS depends on many variables including the wavelength and bandwidth of the input light energy, physical properties of the light carrier medium, and its mechanical dimensions. In general, increasing the diameter of a light guide by a factor of two increases the power threshold for the onset of SBS by a factor of four. SBS originates in a region of the light guide closer to the launch end. If this can be avoided in the larger carrier then the full power launched into it can be coupled into the smaller light carrier further down. The larger diameter of the proximal section allows significantly more power to be coupled to the light guide assembly and transmit to the fiber distal end.

In some embodiments, the proximal light carrier can be a doped optical fiber that improves transmission characteristics and further suppresses the onset of SBS. Some examples of suitable dopants are $GeO_2$, $P_2O_3$, $TiO_2$, $B_2O_3$, $F_2$, $Al_2O_3$. Doped fibers can be much more expensive per unit length than conventional, pure silica fibers.

This approach can allow a short length of an expensive fiber to be used to suppress SBS with a much longer assembly made of lower-cost fiber. Other approaches could implement a short length of photonic crystal fiber, hollow-core fiber, chiral fibers, or similar structured optical fiber in the proximal section and conventional pure fused silica fiber through the longer length of the catheter system 100. This configuration can allow a short length of more expensive fiber to be used in the proximal section with lower costs for the distal section, achieving similar results.

Figure 3A:
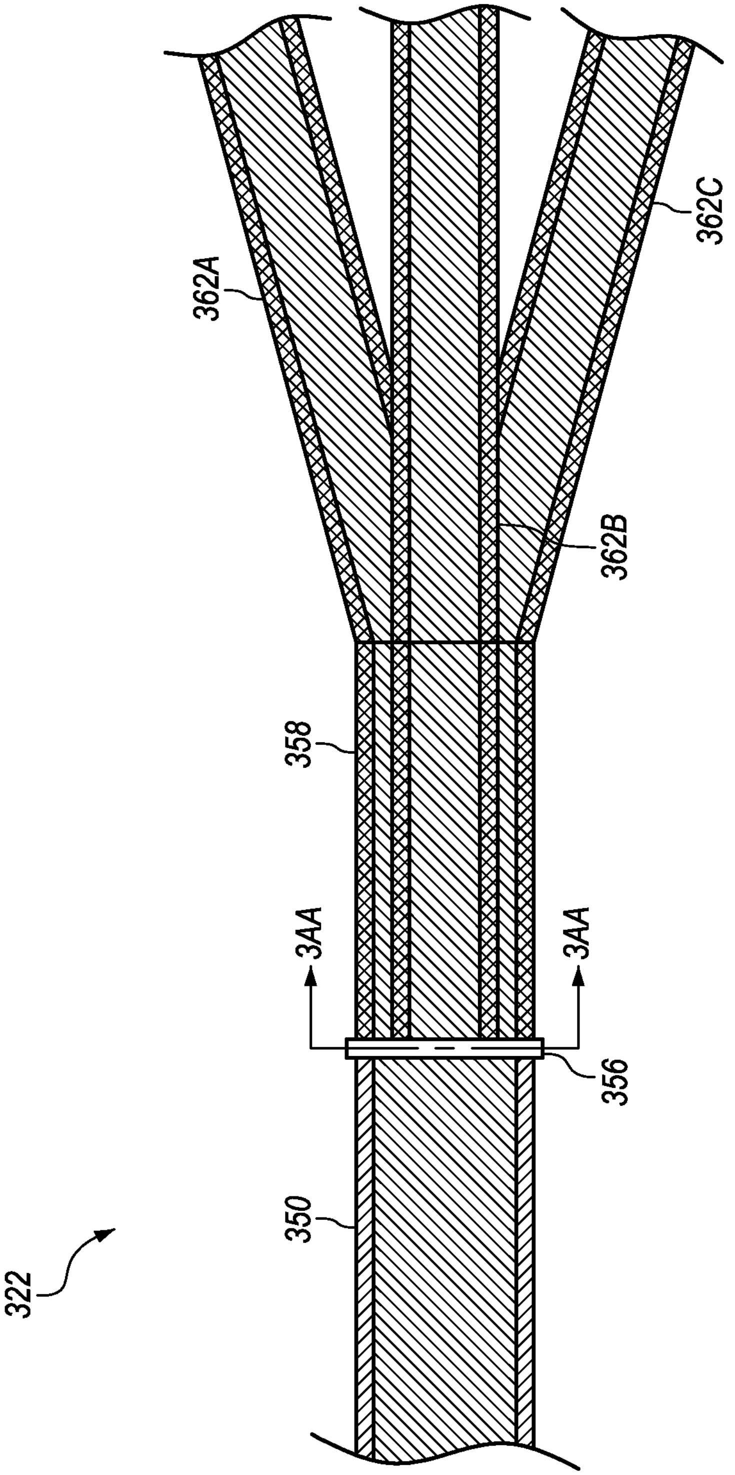
FIG. 3A is a schematic cross-sectional view of one embodiment of a portion of the catheter system including an embodiment of the optical fiber.

FIG. 3A is a schematic cross-sectional view of one embodiment of an optical fiber 322 for use within the catheter system 100. As shown in FIG. 3A the optical fiber 322 can include a first fiber member 350, a fused region 356, a second fiber member 358 including second fiber legs 362A-C. The optical fiber 322 can include any number of second fiber legs 362.

The optical fiber 322 can include a single proximal section joined to a plurality of distal sections. In this embodiment, three distal carriers (e.g., second fiber legs 362A-C) can be fused to a single proximal carrier. The distal carriers can have the same diameter as that used in the proximal section or they can have smaller diameters. In other embodiments, the distal section comprises N light carriers with smaller diameters than the proximal section.

The transmission coupling efficiency can be maximized when the combined end face area of the distal section equals that of the proximal section, $D_d = D_p/\sqrt{N}$. As a result, a 200/220 μm core/cladding light carrier matches well with three 105/125 μm carriers as illustrated in FIG. 3A. The transmission coupling efficiency can be further optimized by thinning the cladding (not shown) on the distal carriers near the fused region 356 to bring the cores closer together and better match with the core of the proximal section. Compressing the region where the cores are joined during fusing can improve overlap.

One advantage of the embodiment illustrated in FIG. 3A is that it eliminates the need to split the energy source into two separate beams and couple each of the beams into separate light carriers when powering two emitters 260 simultaneously. This embodiment can have another advantage of simplifying multiplexer architecture and optics. The embodiment shown in FIG. 3A can also reduce the losses from having two separate beam paths and separate Fresnel losses occurring at the end face of two light carriers.

While there may be sizeable losses in a fused splitter (e.g., the fused region 356), these losses can be comparable to losses in a two-leg multiplexer architecture with complex coupling optics. The fused splitter can simplify multiplexer architecture, can reduce the alignment tolerances allowing simpler optics with improved transmission, and can eliminate losses due to splitting optics and the launch interface.

Figure 3B:
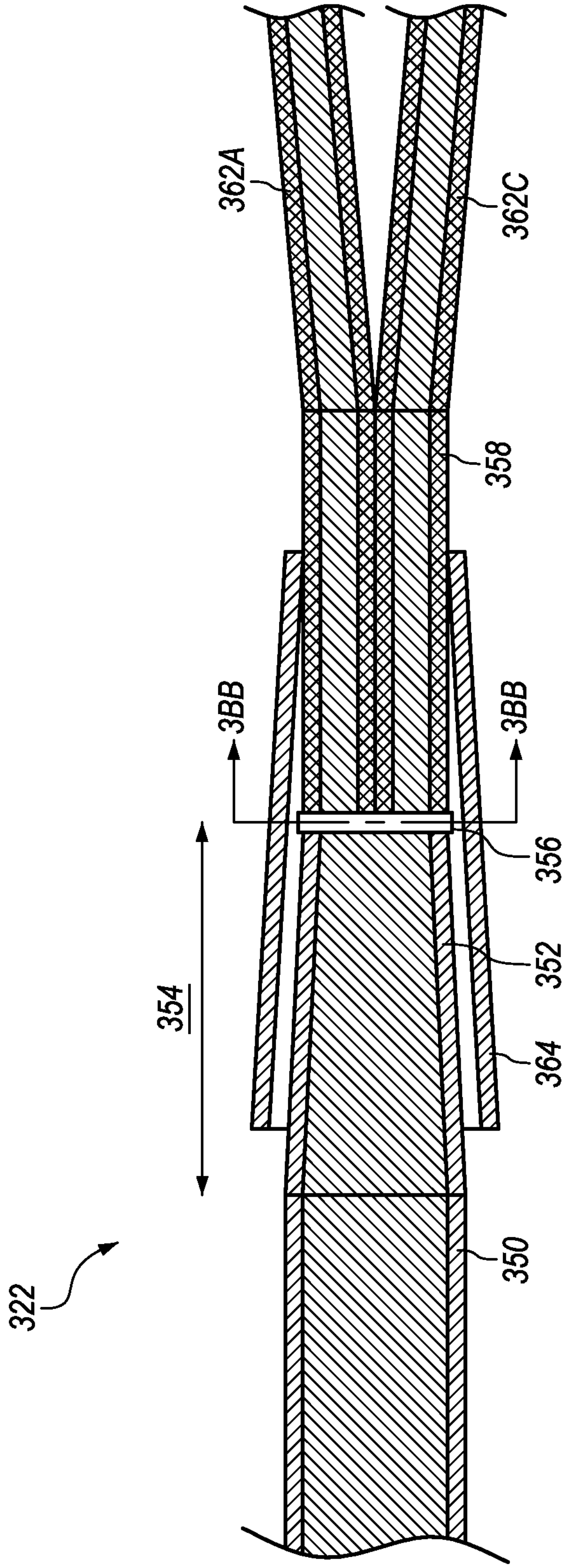
FIG. 3B is a schematic cross-sectional view of another embodiment of another optical fiber for use within a catheter system.
Figure 3A:
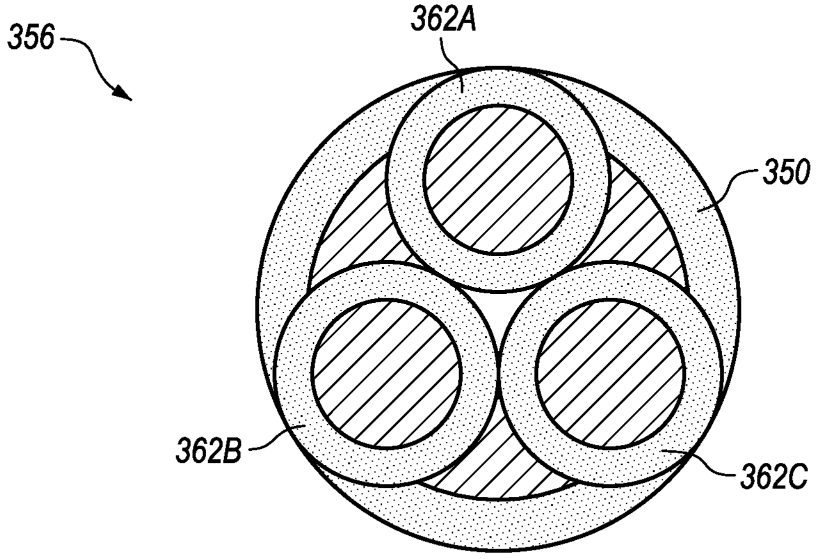
Figure 3B:
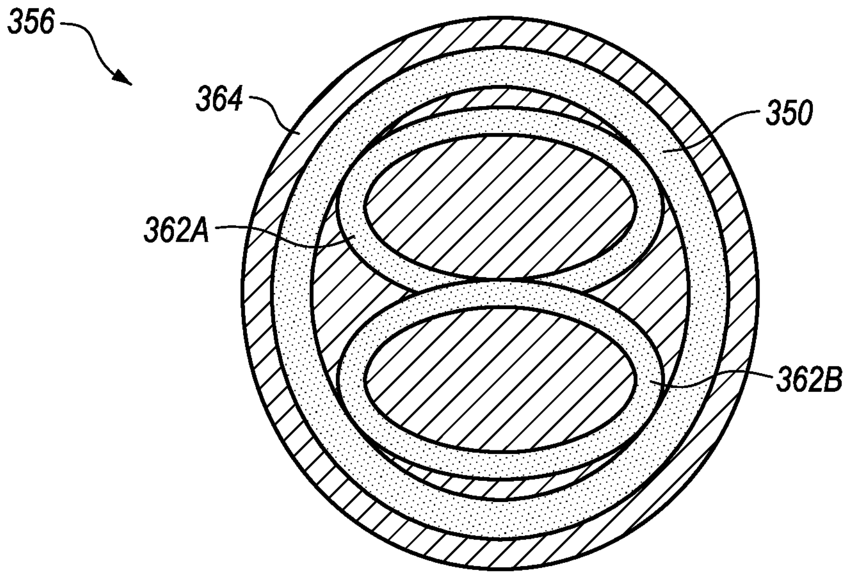

FIG. 3B is a schematic cross-sectional view of another embodiment of another optical fiber 322 for use within the catheter system 100. The embodiment shown in FIG. 3B illustrates a highly optimized 1×2 splitter that transitions from a 200 μm core proximal section to two 105 μm core distal sections. The transition between sections can be optimized by tapering the proximal light carrier to have an area equal to two times that of a 105 μm carrier. The two distal carriers can be formed to better match up with the fiber proximal end.

A separate capillary 364 can be placed around the fused assemblage (e.g., the fused region 356) and fused to optimize the cross-section and the area matching. This approach can be used to improve coupling efficiency for any number of carriers in the splitter. The capillary 364 can be drawn to tight tolerances and can be suitable for use in the catheter system 100. The capillary 364 can vary depending on the design requirements of the catheter system 100 and/or the optical fiber 322. It is understood that the capillary 364 can include additional systems, subsystems, components, and elements than those specifically shown and/or described herein. Additionally, or alternatively, the capillary 364 can omit one or more of the systems, subsystems, and elements that are specifically shown and/or described herein.

FIG. 3AA is a cross-sectional view of the optical fiber taken on line 3AA-3AA in FIG. 3A. As illustrated in FIG. 3AA, the cross-sectional view demonstrates that the fused region 356 can include the first fiber member 350 and the second fiber member legs 362A-C. The first fiber member 350 can be fused to the second fiber member legs 362A-C at different locations so that portions of the outer perimeter of the first fiber member 350 is fused to portions the outer perimeter of the second fiber leg 362A, the second fiber leg 362B, and the second fiber leg 362C.

FIG. 3BB is a cross-sectional view of the optical fiber taken on line 3BB-3BB in FIG. 3B. As illustrated in FIG. 3BB, the cross-sectional view demonstrates that the fused region 356 can include the first fiber member 350 and the second fiber member legs 362A-B. The fused region 356 can be substantially surrounded by the capillary 364.

Figure 4A:
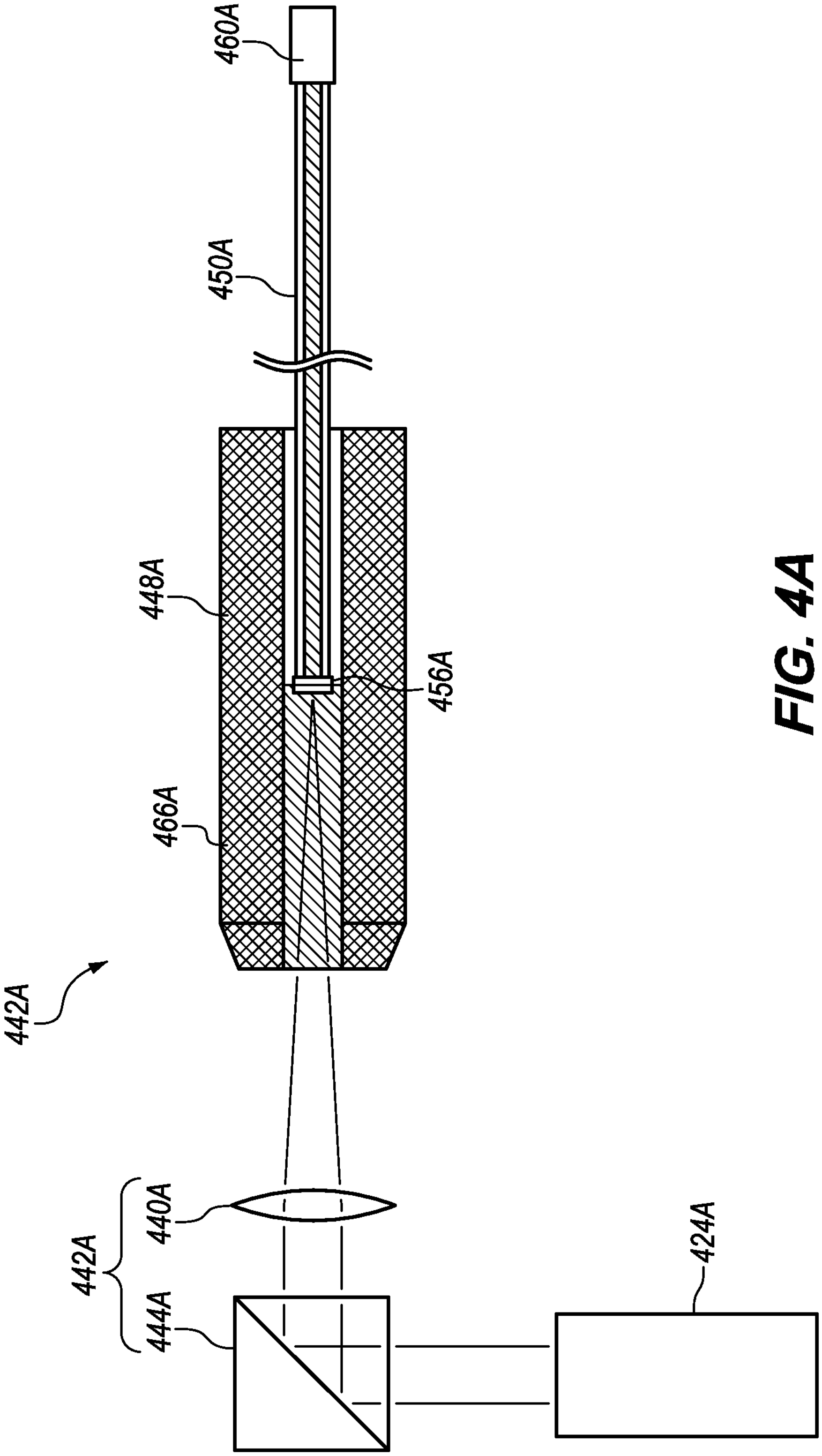
FIG. 4A is a schematic cross-sectional view of another embodiment of the catheter system including an embodiment of the optical fiber, the coupling optics, and the energy source.

FIG. 4A is a schematic cross-sectional view of another embodiment of the optical fiber 422A, the coupling optics 442A (e.g., a reflector 444A and a lens 446A), and the energy source (e.g., a laser 424A) for use within the catheter system 100 (illustrated in FIG. 1). In some embodiments, the optical fiber 422A can include a ferrule 448A, a first fiber member 450A, a fused region 456A, an emitter 460A, and an endcap 466A.

The endcap 466A can provide a larger surface area to spread the converging incident beam over before it focuses down the energy source to couple into the light carrier. The shape, configuration and size of the endcap 466A can vary depending on the design requirements of the catheter system 100 and/or the optical fiber 422A. In one embodiment, the endcap 466A can have a substantially cylindrical configuration. Alternatively, the endcap 466A can have another suitable configuration.

The embodiment shown in FIG. 4A illustrates a direct approach to improving coupling to the smaller light carriers using the endcap 466A fused to the proximal end. In general, the damage threshold for optical material is much lower at an air interface than within the bulk material, sometimes by an order of magnitude.

This approach can reduce peak irradiance at the surface, thereby increasing the damage threshold for the light carrier assembly. The damage threshold near the end face of the light carrier is close to the bulk threshold for the formation materials. This embodiment allows a significantly greater amount of energy to be coupled into a small diameter light carrier. The converging incident beam can be tightly centered on the endcap 466A and can be tightly aligned within the ferrule 448A to achieve alignment for optimal coupling. In certain embodiments, the tight alignment is necessary to center the converging incident beam on the endcap 466A.

Figure 4B:
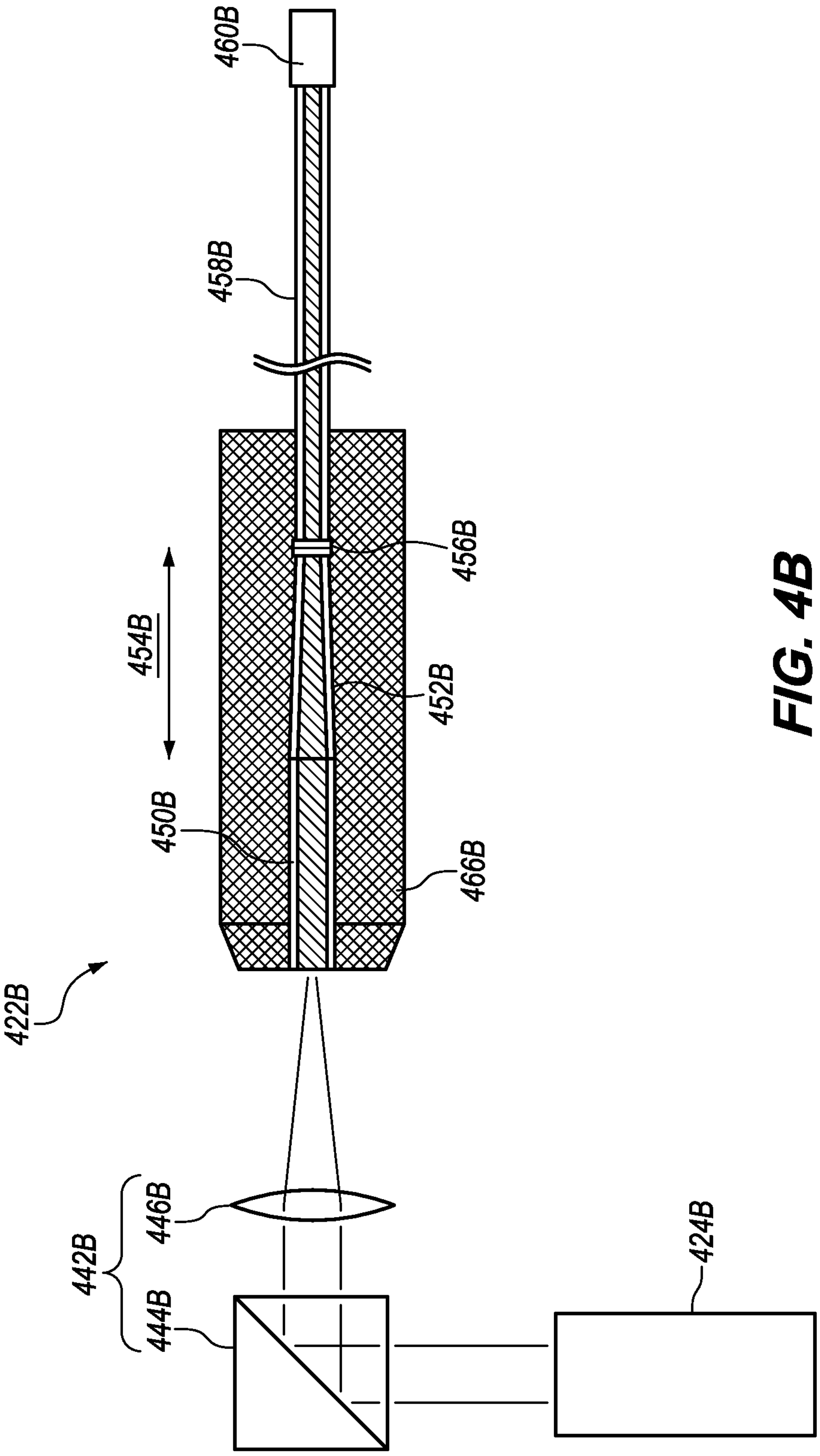
FIG. 4B is a schematic cross-sectional view of another embodiment of the catheter system including another embodiment of the optical fiber, the coupling optics, and the energy source.

FIG. 4B is a schematic cross-sectional view of another embodiment of the optical fiber 422B, the coupling optics 442B, and the energy source (e.g., the laser 424B) for use within the catheter system 100 (illustrated in FIG. 1). The embodiment illustrated in FIG. 4B features a tapered assembly. The tapered light carrier can be a short section (e.g., the tapered portion 452B) confined within the ferrule 456B. This approach can provide a large end face for defocusing the incident beam and coupling high energies thereby increasing the assembly damage threshold. Simultaneously, the embodiment of FIG. 4B can reduce the demands of aligning with the smaller light carrier through the optical guiding of energy through the tapered portion 452B.

The present invention is also directed toward methods for treating a treatment site 106 (illustrated in FIG. 1) within or adjacent to a vessel wall or heart valve, with such methods utilizing the devices disclosed herein.

Fibers

The optical fibers suitable for use herein can include various types of fibers suitable for optical communication with an energy source, such as lasers and lamps. In some embodiments, optical fibers can include fiber connectors and fiber tapers. Fiber tapers can be packaged with a solid metal tube in tens of millimeter length. To convert light from a large core fiber into a small core fiber, fiber tapers that taper a larger core fiber into a smaller core for splicing can be an effective method to minimize the insertion loss. In certain embodiments, fiber tapers can be integrated into fiber connectors and can form a new type of fiber device called a tapered fiber connector.

The fiber connectors can be configured to couple lights from one fiber to another fiber. The fiber connectors can include polished ferrules. The fibers can be encircled into the fiber connectors with epoxy. There are tens of different styles of fiber connectors, including ferrules with an outer diameter of 1.25 mm LC and ones with 2.5 mm SC. The inner diameter of a ferrule depends on the fiber sizes, sometimes between 126~127 μm diameter for single-mode fibers.

In some embodiments, the ferrules described herein can have diameters (both inner diameters and outer diameters) of greater than or equal to 1 μm, 5 μm, 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 220 μm, 240 μm, 260 μm, 280 μm, 300 μm, 320 μm, 340 μm, 360 μm, 380 μm, 400 μm, 420 μm, 440 μm, 460 μm, 480 μm, 500 μm, 520 μm, 540 μm, 560 μm, 580 μm, 600 μm, 620 μm, 740 μm, 760 μm, 780 μm, 800 μm, 850 μm, 900 μm, 1 mm, 1.5 mm, 2.0 mm, 2.5 mm, 3.0 mm, 3.5 mm, 4.0 mm or greater than 4.0 mm. It is appreciated that the ferrules illustrated and/or described herein can have diameters (both inner diameters and outer diameters) that can fall within a range, wherein any of the foregoing numbers can serve as the lower or upper bound of the range, provided that the lower bound of the range is a value less than the upper bound of the range. The ferrules described herein can have diameters (both inner diameters and outer diameters) that fall outside of the range described herein.

For high power laser fiber coupling, a large core diameter fiber can be used to reduce the power density at the fiber coupling surface to enhance the damage threshold. However, a large diameter fiber is not flexible for many applications, such as catheters for medical treatments. In these applications, converting light power from a large diameter fiber into a small diameter fiber is important. Connecting or splicing a large core fiber with a small core fiber can directly result in unacceptable insertion loss.

One embodiment of a method for converting light power includes tapering the larger core diameter fibers to match the smaller core diameter fiber and then splicing the fiber tapers to the small core fibers. However, fiber tapers and splice joints need to be well packaged, usually 3 mm diameter and 50 mm long metal tubing, which is extremely inconvenient in many applications.

By integrating fiber connectors with fiber tapers a new type of fiber connector is created, a tapered fiber connector. This type of fiber connector is regular in size, but a fiber taper is encircled with epoxy. Any suitable type of fiber connectors including all single-mode fiber connectors can be improved into tapered fiber connectors for receiving lights as the transverse offset will not introduce any significant loss.

In various embodiments, fusion splicers can taper fibers and splice the fiber tapers onto small core fibers. In other embodiments, other devices and methods can be used to taper fibers and splice the fiber tapers onto small core fibers. Fibers can be tapered using a hydrogen flame to heat a mid-section of fiber that is held under tension. Fibers can be tapered using known devices and methods within the art.

The fiber tapers and splice joints can be encircled in fiber ferrules with epoxy for polishing. Epoxies that can be used herein include thermal epoxies, room temperature cure epoxies (such as ND353), UV curing epoxies (such as the LOCTITE® 4310 UV adhesive), and other suitable epoxies known within the art. The processing can be simple and low cost and the fiber connectors that are integrated with fiber tapers can be configured for high power laser coupling. One type of fiber connector that can be used is a fiber end-cap for high power laser input and output with reduced power density on fiber surfaces. Fiber end-caps can require accurate alignment as end-cap glass is equivalent to a free space rather than a waveguide. However, fiber tapers can still function as waveguides and thus alignment is not necessary.

In some embodiments, when core/cladding diameters of 200/220 μm fibers are selected to couple high power laser and core/cladding diameters of 105/125 μm fibers are used to build catheters for medical treatments, the process of converting laser power from the large core diameter fibers to the small core fibers is important.

For example, when directly splicing core/cladding diameters of 200/220 μm larger fibers onto core/cladding 105/125 μm smaller fibers together, a large portion of the light will not couple from the large fiber into the small fiber, which results in a high insertion loss. As an estimation, the ratio of two core overlapping is:

$$\left(\frac{105}{200}\right)^2 = 0.275 \quad \text{[Equation 1]}$$

which is about a 6 dB loss. This insertion loss is even higher for higher-order modes as the higher-order modes are likely distributed far from the core central area. The configuration of step-index fibers is shown below, the refractive index of the fiber core $n_1$ is slightly larger than the cladding $n_2$. To form a total internal reflection for a light's propagation along the fiber, the maximum incident angle α must meet the following conditions:

$$\begin{cases} \sin(\alpha) = n1 \cdot \sin(\beta) \\ n1 \cdot \cos(\beta) = n2 \end{cases} \quad \text{[Equation 2]}$$

Simplifying Equations 1 and 2:

$$\sin(\alpha) = \sqrt{n_1^2 - n_2^2} = NA \quad \text{[Equation 3]}$$

NA is the numerical aperture of the fibers, for 0.22 numerical aperture, the maximum incident angle α is 12.7 degrees. For a non-tapered fiber, the angles of light remain unchanged along the fiber and emit at the same angles α. However, for a tapered fiber, the emitting angle will be larger than the incident angle α, depending on the tapering angle and length.

When the incident angle of light is small enough, or the light beam effective NA is significantly smaller than the small fiber $NA_2$, with a certain tapering angle and tapering length, it is possible that the effective NA of the emitting lights from the fiber taper is still within the smaller fiber acceptable angle range of $\arcsin(NA_2)$, 12.7 degrees for 0.22 numerical aperture. The tapering angle δ is expressed as:

$$\delta = \arctan\left(\frac{D_1 - D_2}{2L}\right) \approx \frac{D_1 - D_2}{2L} \quad \text{[Equation 4]}$$

the lights get 2δ angle to increase at every reflection due to the tapered surface. For tapering core diameter of 200 μm large fiber going into a 105 μm small core with a 4 mm taper length makes the tapering angle δ=0.68 degree. For tapering single-mode fibers, in order to keep the fundamental mode in the fiber virtually unchanged, the adiabatic tapers require the tapering angle to be small enough 0.35 degrees for SMF28. For multimode power coupling, the tapering angle could be larger, but it can keep lights from leaking into the cladding.

In certain embodiments, when a 3 mm diameter parallel free-space laser beam is focused by a 50 mm focal lens and coupled to a fiber taper, the NA of the incident beam is:

$$NA = \arctan\left(\frac{3}{2 \times 50}\right) = 0.03 \sim 1.72^\circ \quad \text{[Equation 5]}$$

The light angles increase by 2δ for every reflection at the surface of fiber tapers, thus the pitches between two reflections along the fiber become shorter and shorter while the angles become larger and larger. In order to prevent light leaking from the fiber core to the cladding, the largest angle of lights must be not more than $\arcsin(NA_2)$.

When a 3 mm diameter free space laser beam is focused by a lens with 50 mm focal length, tapering a 200 μm large diameter fiber into a small core 105 μm (fiber taper 200/105 μm), the fiber taper can convert all lights from the large core fiber into 105 μm small core fiber with no light leakage to the fiber cladding at the tapering area and the splice joint.

For tapering large diameters of 200 μm, 300 μm, and 400 μm into a 105 μm small core with a 5 mm taper length, simulations show all light from larger core diameter fibers can be fully coupled to the small core fibers like an optical funnel. For fiber tapers of 1000/105 μm and a 5 mm taper length, simulations show light leakage from the fiber core to the cladding, which results in a significant insertion loss as shown below. For fiber tapers of 200/105 μm, simulations also show that the light-emitting angle with respect to the taper length is curved. The smaller angles or beam sizes are usually desired and thus the optimized taper length is at least 4~5 mm.

In some embodiments, 500 μm core diameters can be tapered into a 105 μm small core for light conversion. However, simulations show that the tapering length must be longer than 5 mm to avoid lights leaking into the cladding. The taper length can be 15 mm long for achieving a smaller emitting angle.

A fiber fusion splicer FSM100P can taper fibers from up to 500 μm large fibers into a small size. Comparing with a 105/125 μm fiber for high power light coupling, large-diameter fibers can significantly reduce the power density. For tapered connectors with fiber tapers with diameters of 200 μm, 300, 400 μm, and 500 μm, the power densities can be reduced by ~4, 8, 15, and 22 times, respectively. Fusing fiber for tapering can expand the fiber core slightly, fiber core diameters can be tapered to be slightly smaller, e.g. taper 200 μm core diameter to ~95 μm core for matching 105/125 μm fibers.

In some embodiments, the optical fibers and/or light carriers described herein can have diameters of greater than or equal to 1 μm, 5 μm, 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, 160 μm, 170 μm, 180 μm, 190 μm, 200 μm, 220 μm, 240 μm, 260 μm, 280 μm, 300 μm, 320 μm, 340 μm, 360 μm, 380 μm, 400 μm, 420 μm, 440 μm, 460 μm, 480 μm, 500 μm, 520 μm, 540 μm, 560 μm, 580 μm, 600 μm, 620 μm, 740 μm, 760 μm, 780 μm, 800 μm, 850 μm, 900 μm, 1 mm, 1.5 mm, 2.0 mm, 2.5 mm, 3.0 mm or greater than 3.0 mm. It is appreciated that the optical fibers and/or light carriers illustrated and/or described herein can have diameters that can fall within a range, wherein any of the foregoing numbers can serve as the lower or upper bound of the range, provided that the lower bound of the range is a value less than the upper bound of the range. The optical fibers and/or light carriers described herein can have diameters that fall outside of the range described herein.

In various embodiments, the optical fibers and/or light carriers described herein can have taper lengths of greater than or equal to 0.5 mm, 1.0 mm, 1.5 mm, 2.0 mm, 2.5 mm, 3.0 mm, 3.5 mm, 4.0 mm, 4.5 mm, 5.0 mm, 5.5 mm, 6.0 mm, 6.5 mm, 7.0 mm, 7.5 mm, 8.0 mm, 8.5 mm, 9.0 mm, 9.5 mm, 10.0 mm, 11.0 mm, 12.0 mm, 13.0 mm, 14.0 mm, 15.0 mm, 20 mm, 25 mm, 30 mm or greater than 30 mm. It is appreciated that the optical fibers and/or light carriers illustrated and/or described herein can have taper lengths that can fall within a range, wherein any of the foregoing numbers can serve as the lower or upper bound of the range, provided that the lower bound of the range is a value less than the upper bound of the range. The optical fibers and/or light carriers described herein can have taper lengths that fall outside of the range described herein.

Lasers

The lasers suitable for use herein can include various types of lasers including lasers and lamps. Suitable lasers can include short pulse lasers on the sub-millisecond timescale. In some embodiments, the laser can include lasers on the nanosecond (ns) timescale. The lasers can also include short pulse lasers on the picosecond (ps), femtosecond (fs), and microsecond (us) timescales. It is appreciated that there are many combinations of laser wavelengths, pulse widths, and energy levels that can be employed to achieve plasma in the balloon fluid of the catheters illustrated and/or described herein. In various embodiments, the pulse widths can include those falling within a range including from at least 10 ns to 200 ns. In some embodiments, the pulse widths can include those falling within a range including from at least 20 ns to 100 ns. In other embodiments, the pulse widths can include those falling within a range including from at least 1 ns to 5000 ns.

Exemplary nanosecond lasers can include those within the UV to IR spectrum, spanning wavelengths of about 10 nanometers to 1 millimeter. In some embodiments, the lasers suitable for use in the catheter systems herein can include those capable of producing light at wavelengths of from at least 350 nm to 2000 nm. In some embodiments, the lasers can include those capable of producing light at wavelengths of from at least 700 nm to 3000 nm. In some embodiments, the lasers can include those capable of producing light at wavelengths of from at least 100 nm to 10 micrometers (μm). Nanosecond lasers can include those having repetition rates of up to 200 kHz. In some embodiments, the laser can include a Q-switched thulium:yttrium-aluminum-garnet (Tm:YAG) laser. In some embodiments, the laser can include a neodymium:yttrium-aluminum-garnet (Nd:YAG), holmium:yttrium-aluminum-garnet (Ho:YAG), erbium:yttrium-aluminum-garnet (Er:YAG), excimer laser, helium-neon laser, carbon dioxide laser, as well as doped, pulsed, fiber lasers.

Pressure Waves

The catheters illustrated and/or described herein can generate pressure waves having maximum pressures in the range of at least 1 megapascal (MPa) to 100 MPa. The maximum pressure generated by a particular catheter will depend on the laser, the absorbing material, the bubble expansion, the propagation medium, the balloon material, and other factors. In some embodiments, the catheters illustrated and/or described herein can generate pressure waves having maximum pressures in the range of at least 2 MPa to 50 MPa. In other embodiments, the catheters illustrated and/or described herein can generate pressure waves having maximum pressures in the range of at least 2 MPa to 30 MPa. In yet other embodiments, the catheters illustrated and/or described herein can generate pressure waves having maximum pressures in the range of at least 15 MPa to 25 MPa. In some embodiments, the catheters illustrated and/or described herein can generate pressure waves having peak pressures of greater than or equal to 1 MPa, 2 MPa, 3 MPa, 4 MPa, 5 MPa, 6 MPa, 7 MPa, 8 MPa, 9 MPa, 10 MPa, 11 MPa, 12 MPa, 13 MPa, 14 MPa, 15 MPa, 16 MPa, 17 MPa, 18 MPa, 19 MPa, 20 MPa, 21 MPa, 22 MPa, 23 MPa, 24 MPa, or 25 MPa, 26 MPa, 27 MPa, 28 MPa, 29 MPa, 30 MPa, 31 MPa, 32 MPa, 33 MPa, 34 MPa, 35 MPa, 36 MPa, 37 MPa, 38 MPa, 39 MPa, 40 MPa, 41 MPa, 42 MPa, 43 MPa, 44 MPa, 45 MPa, 46 MPa, 47 MPa, 48 MPa, 49 MPa, or 50 MPa. It is appreciated that the catheters illustrated and/or described herein can generate pressure waves having operating pressures or maximum pressures that can fall within a range, wherein any of the foregoing numbers can serve as the lower or upper bound of the range, provided that the lower bound of the range is a value less than the upper bound of the range.

Therapeutic treatment can act via a fatigue mechanism or a brute force mechanism. For a fatigue mechanism, operating pressures would be about at least 0.5 MPa to 2 MPa, or about 1 MPa. For a brute force mechanism, operating pressures would be about at least 20 MPa to 30 MPa, or about 25 MPa. Pressures between the extreme ends of these two ranges may act upon a treatment site using a combination of a fatigue mechanism and a brute force mechanism.

The pressure waves described herein can be imparted upon the treatment site from a distance within a range from at least 0.01 millimeters (mm) to 25 mm extending radially from a longitudinal axis of a catheter placed at a treatment site. In some embodiments, the pressure waves can be imparted upon the treatment site from a distance within a range from at least 1 mm to 20 mm extending radially from a longitudinal axis of a catheter placed at a treatment site. In other embodiments, the pressure waves can be imparted upon the treatment site from a distance within a range from at least 0.1 mm to 10 mm extending radially from a longitudinal axis of a catheter placed at a treatment site. In yet other embodiments, the pressure waves can be imparted upon the treatment site from a distance within a range from at least 1.5 mm to 4 mm extending radially from a longitudinal axis of a catheter placed at a treatment site. In some embodiments, the pressure waves can be imparted upon the treatment site from a range of at least 2 MPa to 30 MPa at a distance from 0.1 mm to 10 mm. In some embodiments, the pressure waves can be imparted upon the treatment site from a range of at least 2 MPa to 25 MPa at a distance from 0.1 mm to 10 mm. In some embodiments, the pressure waves can be imparted upon the treatment site from a distance that can be greater than or equal to 0.1 mm, 0.2 mm, 0.3 mm, 0.4 mm, 0.5 mm, 0.6 mm, 0.7 mm, 0.8 mm, or 0.9 mm, 1 mm, 2 mm, 3 mm, 4 mm, 5 mm, 6 mm, 7 mm, 8 mm, 9 mm, or 10 mm, or can be an amount falling within a range between, or outside the range of any of the foregoing.

The systems and methods described herein provide improved optical coupling to an individual light carrier that is organized in a multi-channel array. The advantage of the improved optical coupling is to increase the damage threshold and coupling efficiency while reducing demand on mechanical tolerances.

The systems and methods provided herein improve an optical damage threshold and energy throughput while maintaining a small diameter section leading to the plasma generator. The advantage of the improved optical damage threshold and energy throughput is to minimize the mechanical cross-section and bending stiffness of the light guide bundle and catheter.

The systems and methods provided herein allow the use of larger light carriers in the proximal section of the single-use device (sometimes referred to herein as a "SUD") that are easy to align optics with to couple light into while allowing smaller carriers to be used to in the distal section to optimize key mechanical characteristics such as crossing the profile and bending stiffness. Advantages of this approach are that it: 1) reduces demand on the connector tolerances for alignment of the light carrier to the coupling optics and mechanical tolerances of their location in a multi-channel array, 2) reduces system performance dependence on the accuracy of connecting and aligning the multi-channel array to the multiplexer, 3) reduces dependence on the accuracy of the positioning mechanism in the multiplexer and associated quality and precision of its optical and mechanical components, 4) makes it possible to use lower-cost, lower accuracy ferrules on the SUD, reducing costs, 5) increases optical damage threshold at the proximal end face of the light carrier allowing increased energy to drive the emitters, and 6) reduces transmission losses in the light carrier that are due to non-linear optical processes that increase with the decrease in light carrier diameter.

The systems and methods described herein reduce the optical coupling dependence on the precision and mechanical tolerance stack-ups of assemblies and true alignment for light carrier(s), ferrule(s), connector(s), and receptacle(s), thereby making it possible to use low-cost, low-precision components on the SUD and improve the cost of goods sold.

The systems and methods described herein reduce the multiplexer performance dependence on the accuracy of the positioning mechanism and the associated quality and precision of its optical and mechanical components, thereby improving the speed and performance of the multiplexer and the multi-channel ferrule system.

The systems and methods described herein increase the damage threshold of the light carrier(s) and allow higher energies to be coupled into the light carrier(s) and to the emitter(s) while enabling the use of smaller carrier(s) through the critical sections of the catheter.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

As used herein, the recitation of numerical ranges by endpoints shall include all numbers subsumed within that range, inclusive (e.g., 2 to 8 includes 2, 2.1, 2.8, 5.3, 7, 8, etc.).

It is recognized that the figures shown and described are not necessarily drawn to scale, and that they are provided for ease of reference and understanding, and for relative positioning of the structures.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter systems have been illustrated and described herein, one or more features of any one embodiment can be combined with one or more features of one or more of the other embodiments, provided that such combination satisfies the intent of the present invention.

While a number of exemplary aspects and embodiments of the catheter systems have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope, and no limitations are intended to the details of construction or design herein shown.

What is claimed is:

1. A catheter system for treating a treatment site within or adjacent to a vessel wall or a heart valve, the catheter system comprising:

an inflatable balloon;

an optical fiber including a first fiber member and a second fiber member, the first fiber member having a first fiber member distal region coupled to a second fiber member proximal region, wherein the first fiber member distal region is outside of the inflatable balloon, and wherein the optical fiber has an optical fiber proximal end and an optical fiber distal end positioned within the inflatable balloon, the optical fiber being configured to receive an energy pulse to generate a plasma pulse within the inflatable balloon, the optical fiber including a tapered portion located in the first fiber member between the optical fiber proximal end and the optical fiber distal end that is tapered in a direction toward the optical fiber distal end, the tapered portion being proximal of the inflatable balloon and spaced apart from the optical fiber proximal end and from the optical fiber distal end, wherein the optical fiber includes a first portion positioned proximal to the tapered portion and a second portion positioned distal to the tapered portion, wherein the first portion includes a first constant diameter and wherein the second portion includes a second constant diameter smaller than the first constant diameter; and an energy source that is in optical communication with the fiber proximal end of the optical fiber.

2. The catheter system of claim 1 wherein the second fiber member is positioned within the inflatable balloon.

3. The catheter system of claim 1 wherein the first fiber member is fused to the second fiber member at a fused region.

4. The catheter system of claim 3 further comprising a ferrule that encircles the fused region.

5. The catheter system of claim 4 wherein the ferrule is formed from one of a plastic and a metal.

6. The catheter system of claim 4 wherein the ferrule is configured to encircle only the optical fiber.

7. The catheter system of claim 4 wherein the ferrule is one of a multi-fiber MT ferrule and an MTP ferrule.

8. The catheter system of claim 3 wherein the fused region is outside of the inflatable balloon.

9. The catheter system of claim 1 wherein the first fiber member and the second fiber member are formed as a unitary structure.

10. The catheter system of claim 1 wherein the second fiber member has a second fiber member proximal region that is positioned outside of the inflatable balloon.

11. The catheter system of claim 1 wherein the first fiber member includes an endcap.

12. The catheter system of claim 1 wherein the optical fiber is tapered from a diameter of at least 150 micrometers (μm) down to a diameter of less than 120 micrometers (μm).

13. The catheter system of claim 1 wherein the tapered portion has a tapered portion length of at least 2 millimeters (mm).

14. The catheter system of claim 1 wherein the energy source includes a laser.

15. A catheter system for treating a treatment site within or adjacent to a vessel wall or a heart valve, the catheter system comprising:

an inflatable balloon;

an optical fiber that is configured to receive an energy pulse to generate a plasma pulse within the inflatable balloon, the optical fiber including (i) a first fiber member including a fiber proximal end, (ii) a second fiber member including a fiber distal end that is positioned within the inflatable balloon, (iii) a fused region wherein a distal region of the first fiber member is fused to a proximal region of the second fiber member such that the second fiber member extends distally from the first fiber member, wherein the first fiber member distal region is outside the inflatable balloon, and (iv) a tapered portion located in the first fiber member between the fiber proximal end and the fiber distal end that is tapered in a direction toward the fiber distal end, the tapered portion and spaced apart from the fiber proximal end and from the fiber distal end, wherein the optical fiber includes a first portion positioned proximal to the tapered portion and a second portion positioned distal to the tapered portion, wherein the first portion includes a first constant diameter and wherein the second portion includes a second constant diameter smaller than the first constant diameter.

16. The catheter system of claim 15 wherein the optical fiber further includes a ferrule that encircles at least the fused region.

17. The catheter system of claim 15 wherein the fused region is outside of the inflatable balloon.

* * * * *